US012765958B2

(12) United States Patent
Bagheri Ghavifekr et al.

(10) Patent No.: US 12,765,958 B2
(45) Date of Patent: Oct. 20, 2026

(54) ROBOTIC MICROSURGERY ASSEMBLY, OPERATING ARENA AND METHOD

(71) Applicant: MEDICAL MICROINSTRUMENTS, INC., Pisa (IT)

(72) Inventors: Matteo Bagheri Ghavifekr, Pisa (IT); Nicola Pineschi, Pisa (IT); Massimiliano Simi, Pisa (IT); Giuseppe Maria Prisco, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 819 days.

(21) Appl. No.: 17/760,476

(22) PCT Filed: Feb. 9, 2021

(86) PCT No.: PCT/IB2021/051029

§ 371 (c)(1),
(2) Date: Aug. 10, 2022

(87) PCT Pub. No.: WO2021/161162

PCT Pub. Date: Aug. 19, 2021

(65) Prior Publication Data

US 2023/0092748 A1 Mar. 23, 2023

(30) Foreign Application Priority Data

Feb. 10, 2020 (IT) ........................ 102020000002548

(51) Int. Cl.
*A61B 34/37* (2016.01)
*A61B 17/00* (2006.01)
(Continued)

(52) U.S. Cl.
CPC .............. *A61B 34/37* (2016.02); *A61B 34/20* (2016.02); *A61B 34/74* (2016.02); *A61B 50/13* (2016.02);
(Continued)

(58) Field of Classification Search
CPC ......... A61B 34/37; A61B 34/20; A61B 34/74; A61B 50/13; A61B 90/20; A61B 90/50;
(Continued)

(56) References Cited

U.S. PATENT DOCUMENTS 5,876,325 A 3/1999 Mizuno et al.
6,731,988 B1 5/2004 Green
(Continued)

FOREIGN PATENT DOCUMENTS

CN 106175851 A 12/2016
CN 206651871 U 11/2017
(Continued)

OTHER PUBLICATIONS

International Search Report and Written Opinion for International Patent Application No. PCT/IB2021/051029, mailed Apr. 23, 2021, 15 pages.

*Primary Examiner* — Amanda L Steinberg
(74) *Attorney, Agent, or Firm* — Armstrong Teasdale LLP

(57) ABSTRACT

A robotic surgery assembly for robotic-aided microsurgery includes at least one transmission component; at least one motorized manipulator including at least one motorized linear slider; and at least one sterile adapter including a coupling device suitable for connecting to a surgical instrument. The transmission component is interposed between the at least one motorized manipulator and at least one sterile adapter, so to rigidly determine at least the relative mutual position of the at least one motorized linear slider of the motorized manipulator and the coupling device sterile adapter.

17 Claims, 10 Drawing Sheets

(51) Int. Cl.
*A61B 34/00* (2016.01)
*A61B 34/20* (2016.01)
*A61B 34/30* (2016.01)
*A61B 50/13* (2016.01)
*A61B 90/20* (2016.01)
*A61B 90/50* (2016.01)

(52) U.S. Cl.
CPC .............. *A61B 90/20* (2016.02); *A61B 90/50* (2016.02); *A61B 2017/00345* (2013.01); *A61B 2017/00398* (2013.01); *A61B 2017/00477* (2013.01); *A61B 2034/2051* (2016.02); *A61B 2034/2055* (2016.02); *A61B 2034/305* (2016.02)

(58) Field of Classification Search
CPC .... A61B 2034/2051; A61B 2034/2055; A61B 2034/305; A61B 2017/00345; A61B 2017/00398; A61B 2017/00477
See application file for complete search history.

(56) References Cited

U.S. PATENT DOCUMENTS 7,331,967 B2 2/2008 Lee et al.
7,886,743 B2 2/2011 Cooper et al.
7,947,050 B2 5/2011 Lee et al.
8,004,229 B2 8/2011 Nowlin et al.
8,005,571 B2 8/2011 Sutherland et al.
8,123,740 B2 2/2012 Madhani et al.
8,220,468 B2 7/2012 Cooper et al.
8,281,670 B2 10/2012 Larkin et al.
8,375,808 B2 2/2013 Blumenkranz et al.
8,521,331 B2 8/2013 Itkowitz
8,540,748 B2 9/2013 Murphy et al.
8,812,160 B2 8/2014 Hagn et al.
8,831,782 B2 9/2014 Itkowitz
8,935,003 B2 1/2015 Itkowitz et al.
8,939,963 B2 1/2015 Rogers et al.
9,060,796 B2 6/2015 Seo
9,101,379 B2 8/2015 Au et al.
9,408,668 B2 8/2016 Durant et al.
9,554,866 B2 1/2017 Cunningham et al.
9,629,680 B2 4/2017 Winer
9,743,989 B2 8/2017 Itkowitz et al.
9,949,799 B2 4/2018 Hingwe et al.
9,968,405 B2 5/2018 Cooper et al.
10,123,844 B2 11/2018 Nowlin et al.
10,219,870 B2 3/2019 Mondry et al.
10,219,898 B2 3/2019 Forsell
10,292,661 B1 5/2019 Laborde
10,299,873 B2 5/2019 Hares et al.
10,307,199 B2 6/2019 Farritor et al.
10,321,964 B2 6/2019 Grover et al.
10,357,320 B2 7/2019 Beira
10,357,324 B2 7/2019 Flatt et al.
10,376,323 B2 8/2019 Farritor et al.
10,376,337 B2 8/2019 Kilroy et al.
10,393,109 B2 8/2019 Wu et al.
10,420,618 B2 9/2019 Grover et al.
10,470,830 B2 11/2019 Hill et al.
10,485,621 B2 11/2019 Morrissette et al.
10,512,514 B2 12/2019 Nowlin et al.
10,531,929 B2 1/2020 Widenhouse et al.
10,561,468 B2 2/2020 Cunningham et al.
10,624,708 B2 4/2020 Hunter
10,639,114 B2 5/2020 Schuh et al.
10,653,489 B2 5/2020 Kopp
10,661,453 B2 5/2020 Koenig et al.
10,736,706 B2 8/2020 Scheib
10,751,136 B2 8/2020 Farritor et al.
10,758,298 B2 9/2020 Felder et al.
10,779,898 B2 9/2020 Hill et al.
10,789,329 B2 9/2020 Lanting
10,813,713 B2 10/2020 Koch, Jr. et al.
10,820,953 B2 11/2020 Kralicky et al.
10,864,051 B2 12/2020 Simi et al.
10,881,477 B1 1/2021 Genova et al.
10,888,390 B2 1/2021 Higuchi et al.
10,898,281 B2 1/2021 Cooper et al.
10,987,192 B2 4/2021 Garcia Kilroy et al.
11,045,268 B2 6/2021 Grover et al.
11,083,534 B2 8/2021 Hares
11,109,925 B2 9/2021 Cooper et al.
11,172,997 B2 11/2021 Kostrzewski et al.
11,179,209 B2 11/2021 Kralicky et al.
11,179,211 B2 11/2021 Zemlok et al.
11,246,670 B2 2/2022 Swayze et al.
11,266,469 B2 3/2022 Fuerst et al.
11,284,957 B2 3/2022 Denlinger et al.
11,344,374 B2 5/2022 Tekiela et al.
11,357,597 B2 6/2022 Jhaveri et al.
11,406,465 B2 8/2022 Zemlok et al.
11,446,097 B2 9/2022 Savall et al.
11,457,987 B2 10/2022 He et al.
11,478,928 B2 10/2022 Hariri
11,484,379 B2 11/2022 Sutherland et al.
11,504,197 B1 11/2022 Noonan et al.
11,504,203 B2 11/2022 Flatt et al.
11,576,733 B2 2/2023 Anglese
11,607,279 B2 3/2023 Chaplin
11,666,401 B2 6/2023 Denlinger et al.
11,684,434 B2 6/2023 Shelton, IV
2006/0087746 A1 4/2006 Lipow
2013/0123798 A1* 5/2013 Tsao ...................... A61B 90/11 606/130
2014/0069437 A1 3/2014 Reis et al.
2014/0179997 A1 6/2014 Grunberg et al.
2017/0252112 A1 9/2017 Crawford et al.
2017/0265949 A1 9/2017 Crawford et al.
2018/0116741 A1 5/2018 Garcia et al.
2018/0250085 A1* 9/2018 Simi ...................... B25J 9/104
2018/0296285 A1 10/2018 Simi et al.
2019/0000580 A1 1/2019 Scheib et al.
2019/0223969 A1 7/2019 Ramstad et al.
2020/0138534 A1 5/2020 Garcia Kilroy et al.
2020/0197112 A1 6/2020 Chin et al.
2020/0214779 A1 7/2020 Masuda et al.
2020/0222134 A1 7/2020 Schuh et al.
2020/0289223 A1 9/2020 Denlinger et al.
2020/0330170 A1 10/2020 Farritor et al.
2020/0397517 A1 12/2020 Unsworth
2020/0405408 A1 12/2020 Shelton, IV et al.
2020/0405434 A1 12/2020 Schuh et al.
2021/0052338 A1 2/2021 Hill et al.
2021/0085301 A1 3/2021 Au et al.
2021/0121260 A1 4/2021 Genova et al.
2021/0153965 A1 5/2021 Lau et al.
2021/0153966 A1 5/2021 Lau et al.
2021/0196413 A1 7/2021 Inoue
2021/0197401 A1 7/2021 Weintraub et al.
2021/0322119 A1 10/2021 Hares
2022/0031415 A1 2/2022 Vargas et al.
2022/0047345 A1 2/2022 Choi et al.
2022/0184823 A1 6/2022 Bonny et al.
2022/0211452 A1 7/2022 Clark et al.
2022/0218418 A1 7/2022 Jolaeimoghaddam et al.
2022/0226056 A1 7/2022 Beckman et al.
2022/0361736 A1 11/2022 Danna et al.
2022/0370163 A1 11/2022 Schuh et al.
2022/0378526 A1 12/2022 Balicki et al.
2022/0378527 A1 12/2022 Basafa et al.
2022/0378533 A1 12/2022 McDiarmid et al.
2022/0395346 A1 12/2022 Ihara et al.
2022/0401162 A1 12/2022 Unsworth
2023/0045591 A1 2/2023 De La Fuente Klein et al.
2023/0149105 A1 5/2023 Thornycroft et al.

FOREIGN PATENT DOCUMENTS

DE 102005031557 A1 1/2007
EP 1815949 A1 8/2007
WO 9729690 A1 8/1997

(56) References Cited

FOREIGN PATENT DOCUMENTS

| | | | |
|---|---|---|---|
| WO | 2016201207 | A1 | 12/2016 |
| WO | 2017064301 | A1 | 4/2017 |
| WO | 2017083253 | A1 | 5/2017 |

* cited by examiner

ROBOTIC MICROSURGERY ASSEMBLY, OPERATING ARENA AND METHOD

CROSS-REFERENCE TO RELATED APPLICATIONS

This application is a National Stage Application of International Patent Application No. PCT/IB2021/051029, having an International Filing Date of Feb. 9, 2021, which claims priority to Italian Application No. 102020000002548, filed Feb. 10, 2020, each of which is hereby incorporated by reference in its entirety.

Field of the Invention

It is an object of the present invention a robotic assembly for surgery.

In particular, the present invention relates to a robotic assembly suitable for robotic-aided microsurgery.

The present invention also relates to a transmission component for a robotic surgery assembly.

The present invention also relates to an operatory arena.

The present invention also relates to a method of positioning of a robotic surgery system.

Background

Robotic surgery apparatuses are generally known in the art and typically comprise a slave robotic central tower (or robotic cart) and a plurality robotic arms extending from the central tower. Each robotic arm comprises a tele-operated robotic motorized positioning system (or manipulator) for moving a surgical end effector distally attached thereto, the surgical end effector is designed to perform surgical procedures to a patient. A master controller is provided to control the slave motorized positioning system and the surgical end effector.

Typically, the central tower of the robot is telescopically extendable in the vertical direction so that to adjust the height of the plurality of robotic arms in respect of the operatory bed. The central tower may also be telescopically extendable in a horizontal direction to move the robotic arms away from the cart. Each robotic arm has a plurality of motorized rotational joints articulating a number of connecting rods so that each arm results extendable from a folded configuration close to the central tower to an extended configuration wherein the most distal connecting rod is at a maximum distance from the central tower. The most distal connecting rod usually carries a sterile adapter for the connection to one surgical endoscopic instrument or to one laparoscopic camera through an interposed sterile draping layer. The choice of the number and the size of the articulated connecting rods allows each robotic arm to assume a particular individual orientation in respect of the horizontal plane. It is also known to hinge the proximal root of each robotic arm to the same telescopic portion of the robotic tower in order to lift all the robotic arms simultaneously. Robotic apparatuses of this type are shown for example in documents US-2019-223969 and US-2011-27777.

Further examples of tele-operated robots are shown in documents US-2006-0087746, U.S. Pat. No. 6,731,988, WO-2016-201207, CN-106175851, EP-1815949 and US-2018-0116741.

One or more robotic surgery arms secured directly to the operatory bed are also known, as shown for example in documents WO-2017-083253, U.S. Pat. No. 5,876,325, WO-97-29690 and US-2014-0069437.

The patient typically lies on an operatory bed located in a sterile operatory arena, for example within an operatory room in a hospital. Usually, a disposable surgical drape wraps parts of the robot in order to protect the sterile environment of the operatory arena from contamination. Sterilization of the robotic system through disposable draping avoids bacterial contamination due to the non-sterile parts of the robotic apparatus.

Microsurgery procedures are carried out in several phases of the reconstruction of biological tissues, such as for example in the execution of blood vessel anastomosis comprising small diameter vessels and nerves, as well as in the reconstruction of anatomic parts after the occurrence of traumatic lesions, in re-vascularization of tissues, reattachment of limbs, in transplantation and replantation procedures. In the field of microsurgery, robotic apparatuses allow a high degree of miniaturization of the surgical instrument when compared to traditional microsurgery and allows at the same time to reduce the transmission of tremor to the slave surgical instrument of the robotic surgery system. Microsurgery is an open surgery technique. Traditional (non-robotic) microsurgery requires the surgeon to operate together with an operating microscope, typically an optical microscope, able to magnify the patient's anatomy and therefore robotic surgery apparatuses for microsurgery are suitably equipped with an operating microscope. Microscope field of view on patient anatomy range typically with magnification and in a size between 20-70 mm. An example of known optical vision system for surgery applications in shown in document DE-102005031557.

Known robotic surgery apparatuses are also suitable for robot-aided laparoscopic surgery, where the surgical instruments and at least one camera are individually inserted inside the patient's body by means of a set of percutaneous trocars, and wherein a visualization screen visualizes the laparoscopic images of the inner patient's body acquired from the camera. An example of robot-aided laparoscopic surgery is shown in document US-2014-0179997.

The operating arena surrounding the operatory bed where a patient's anatomy lies during robotic-aided microsurgery often results crowded due to the presence of the slave part of the robot, the microscope and the entire robotic-aided surgery équipe.

Furthermore, some applications of robotic-aided microsurgery desire the presence of the surgeon within the sterile operatory arena during the robotic-aided surgery. Thereby, during a single intervention, the same micro-surgeon aims to switch from robotic-aided microsurgery to traditional (non-robotic) microsurgery, therefore grabbing in hand traditional microsurgery tools such as tweezers, and then back to the surgeon robotic master console grabbing in hand the master controllers of the robotic system.

It is felt the need of providing a robotic surgery system of improved versatility in respect of known solutions and at the same time able to fit several operative configurations, some of them that could also temporary exclude the use of a robot, without for this reason increasing the complexity of the robotic system or reducing the surgeon's comfort during surgery.

It is felt the need of providing a robotic surgery system that allows the surgeon to switch from robotic-aided microsurgery to non-robotic microsurgery therefore reducing the encumber of the robotic microsurgery system within the field of view of the microsurgeon, without for this reason increasing the volumetric encumber of the slave robotic apparatus or reducing the microsurgeon's comfort during microsurgery.

It is felt the need of providing a robotic surgery system that allows to position at least a couple of robotic instruments with the same and single motion in the open surgical field and under magnified view of the microscope.

It is felt the need of providing a robotic surgery system that allows to precisely move instruments within the same, or partially overlaying, microsurgical workspace.

Documents WO-2017-064301 and U.S. Pat. No. 10,864,051 of the same Applicant disclose, inter alia, a solution of robotic surgery assembly wherein a single robotic arm extends from the robotic cart and comprises at the distal end thereof a pair of slave tele-operated robotic motorized positioning systems, arranged in parallel and connected to the same distal link of the single robotic arm. Said single distal link of the robotic arm has two joints, each joint attaches one of said two motorized positioning systems. Each motorized positioning system comprises three orthogonal motorized sliders for positioning the surgical instrument having a shaft attached distally thereto along an orthogonal set of three directions. The two motorized positioning systems extend converging one another, so that the two tips of the surgical instruments are both contained in a single operating volume. The control system controlling the actuation of the motorized sliders of the pair of converging motorized positioning systems shall take into account also the component of the gravity applied to the sliding element.

Despite advantageous under several points of view, such solution of converging surgical instrument shafts is prone to inconveniences related to the control of the positioning of both the surgical tips within a same working volume, and the motorized manipulators having said motorized sliders are oriented offset with respect to each other.

It is felt the need of simplifying the control over a robotic surgery system, without for this reason losing the ability for the two surgical instruments respectively distally attached thereto to reach the same operative volume.

Solution

It is a scope of the present invention to overcome the drawbacks mentioned with reference to the known art and providing a robotic surgery system particularly suitable for microsurgery.

These and other scopes are achieved by a robotic surgery assembly and an operatory arena as described and claimed herein.

According to an aspect of the invention, a robotic surgery assembly for robotic-aided microsurgery comprises a macro-positioning arm, and a pair of motorized manipulators both attached to a same first link of said macro-positioning arm. The macro-positioning arm may be a passive macro-positioning arm. The same first link may be the most distal link of the macro-positioning arm. The same first link may be a rigid link able to rigidly determine the mutual position and orientation of said pair of motorized manipulators. The passive macro-positioning arm may comprise magnetic brakes as well as electro-magnetic means, for example one or more solenoid valves, for locking/unlocking at least some of said brakes.

According to an aspect of the invention, each motorized manipulator comprises at least three mutually orthogonal motorized linear sliders. Each slider may be associated to a respective guiding element, such as groove and/or a rail. Each manipulator may be a Cartesian manipulator. The two manipulators may be arranged so that they flank one another, and they may be at substantially the same distance from the same first link of the macro-positioning device.

According to an aspect of the invention, each motorized manipulator is connected to a sterile adapter comprising a coupling device suitable for connecting to a surgical instrument. The surgical instrument is preferably detachable from the sterile adapter. The sterile adapter is preferably detachable from the respective manipulator. At least one motor box assembly may be provided interposed between said transmission component and each of said sterile adapters, and the motor box assembly may comprise a roll motor suitable for pivoting the respective surgical instrument comprising said shaft about the axis of longitudinal development of the shaft. The axis of rotation may be eccentric with respect to the shaft.

According to an aspect of the invention, between each motorized manipulator and the respective sterile adapter is interposed a respective transmission component to rigidly determine the relative mutual position and orientation of at least one motorized linear slider of the motorized manipulator and said coupling device of the respective sterile adapter.

The transmission component may define an offset both linear and angular, so that the shaft of each sterile adapter is offset in respect of each and all the sliding directions of said motorized linear sliders of the respective motorized manipulator.

A surgical instrument may be detachably connected to each sterile adapter.

The shafts of the surgical instruments may extend convergingly.

The motorized linear sliders of a first motorized manipulator of said pair of motorized manipulators may be parallel to the motorized linear sliders of a second motorized manipulator of said pair of motorized manipulators.

One of said motorized linear sliders of at least one motorized manipulator of said pair of motorized manipulators may extend vertically.

The shafts of the surgical instruments may extend converging towards each other pointing with respective distal ends forward.

A flexible and/or rigid case may be provided with the purpose of individually encasing each motorized manipulator of said pair of motorized manipulators, said cases may be distanced one another in an horizontal direction so that a window is delimited at least partially by said two cases. Said same first link of the macro-positioning arm and said pair of encased motorized manipulators form a reversed-“U”-shaped structure partially delimiting said window.

A distal rotational joint may connect midway said same first link to a second, proximal link of the macro-positioning arm, so that a pivoting action pivoting the same first link about the distal rotational joint of a pivoting angle, determines the motorized manipulators to flip their position in respect to the second link of the macro-positioning arm.

The macro-positioning arm may be connected to a robotic cart having at least one ground contact unit, such as a plurality of wheels. The cart may include a top portion having a polygonal shape and defining a top portion perimeter forming a plurality of corner portions wherein said macro-positioning arm is connected to, through an interposed vertical link, near one of said corner portions, in other words the macro-positioning arm is not connected in the geometric center of the cart so that the robot is directional and so that to minimize the distance between the same first link of the macro-positioning arm and the operatory table.

According to an embodiment, an operating arena comprises at least one robotic surgery assembly, an operatory table, and a microscope assembly, wherein at least one ocular of the microscope assembly is at least partially within said window define between said two motorized manipulators.

According to an embodiment, an operating arena comprises at least one robotic surgery assembly and an operatory table, and a screen for visualizing the operatory field.

FIGURES

Further characteristics and advantages of the assembly and of the component will be apparent from the following description provided below of preferred embodiments thereof, given by way of non-limiting examples, with reference to the attached figures, in which.

DETAILED DESCRIPTION OF SOME EMBODIMENTS

Figure 1:
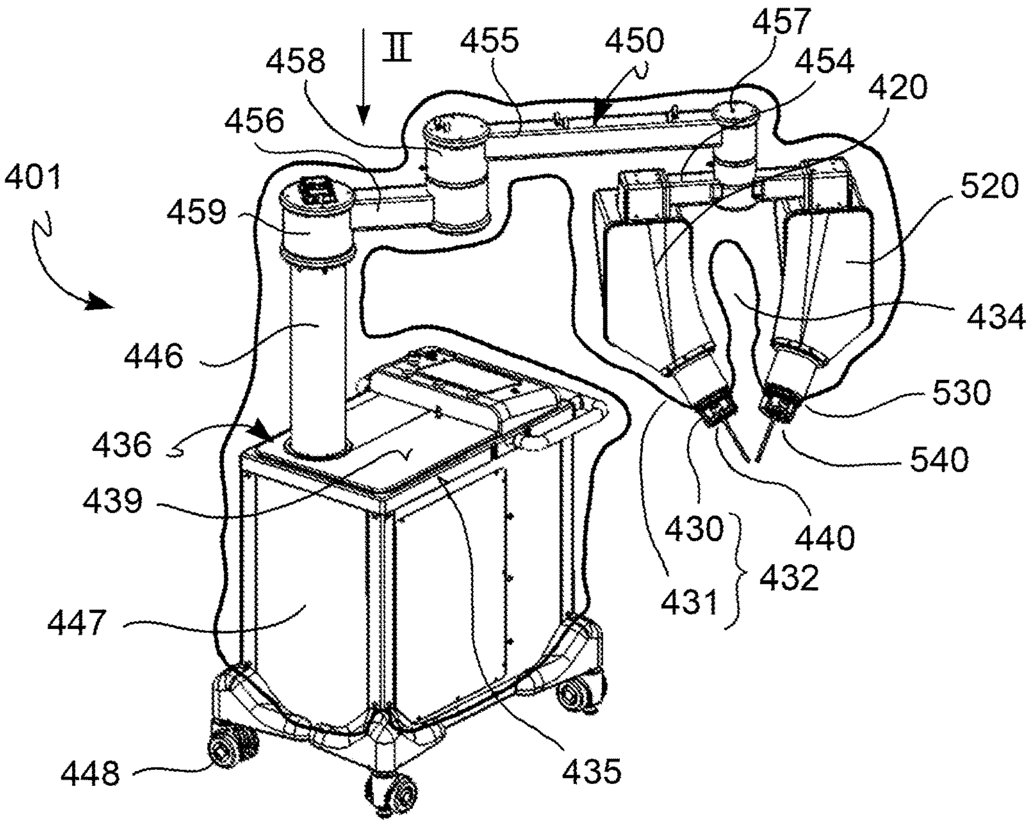
FIG. 1 is an axonometric view of a robotic surgery assembly, according to an embodiment.
Figure 2:
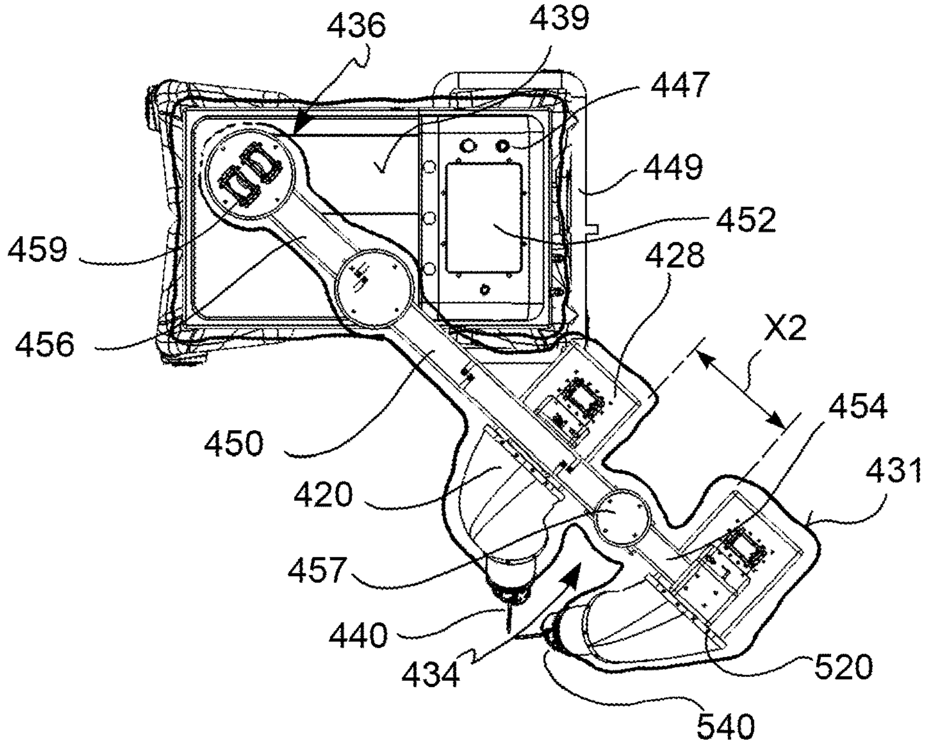
FIG. 2 is a top view from the point of view indicated by arrow II of FIG. 1.
Figure 3:
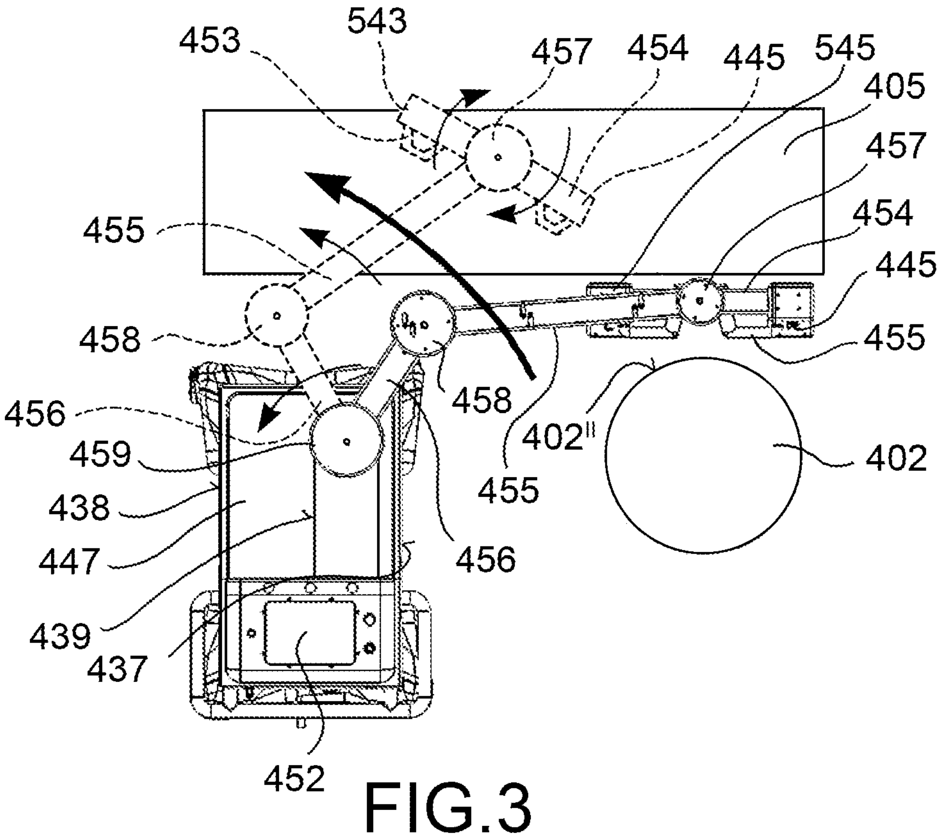
FIG. 3 is a sketch depicting as top view a robotic surgery assembly, according to an embodiment, in an operative condition, wherein the first side of the robotic cart faces the surgeon, and wherein in dotted line is shown a macro-positioning arm in a transitional position.
Figure 4:
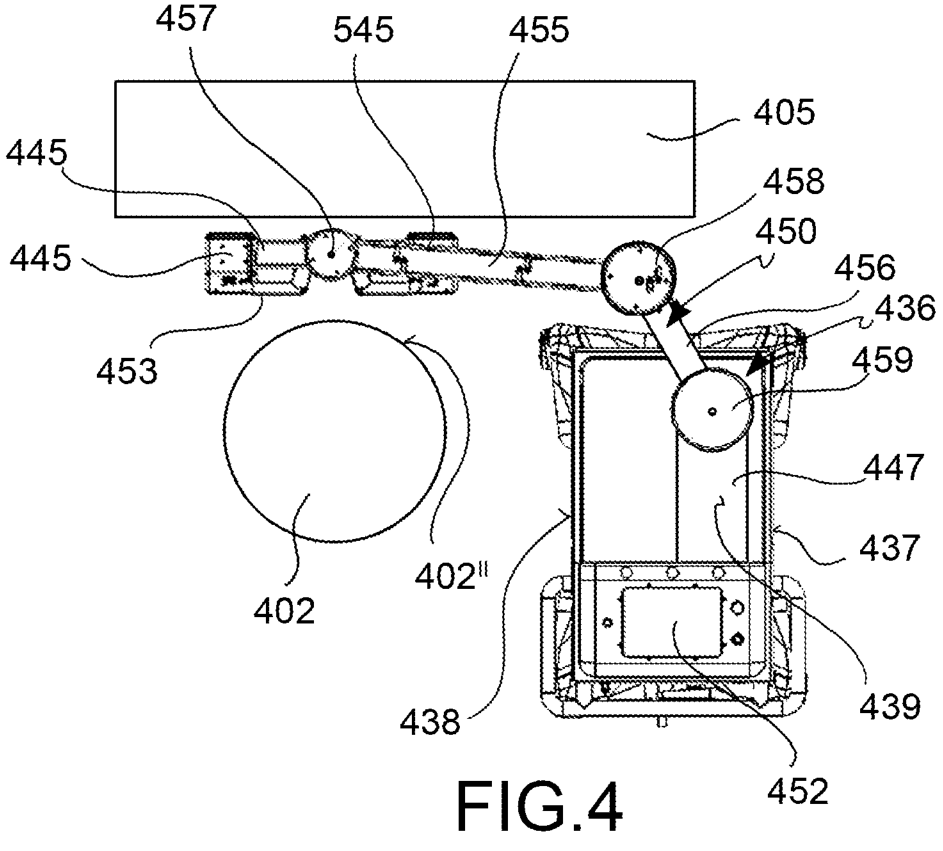
FIG. 4 is a sketch as FIG. 3 depicting the robotic surgery assembly in a an operative condition wherein the second opposite side of the robotic cart faces the surgeon.
Figure 5:
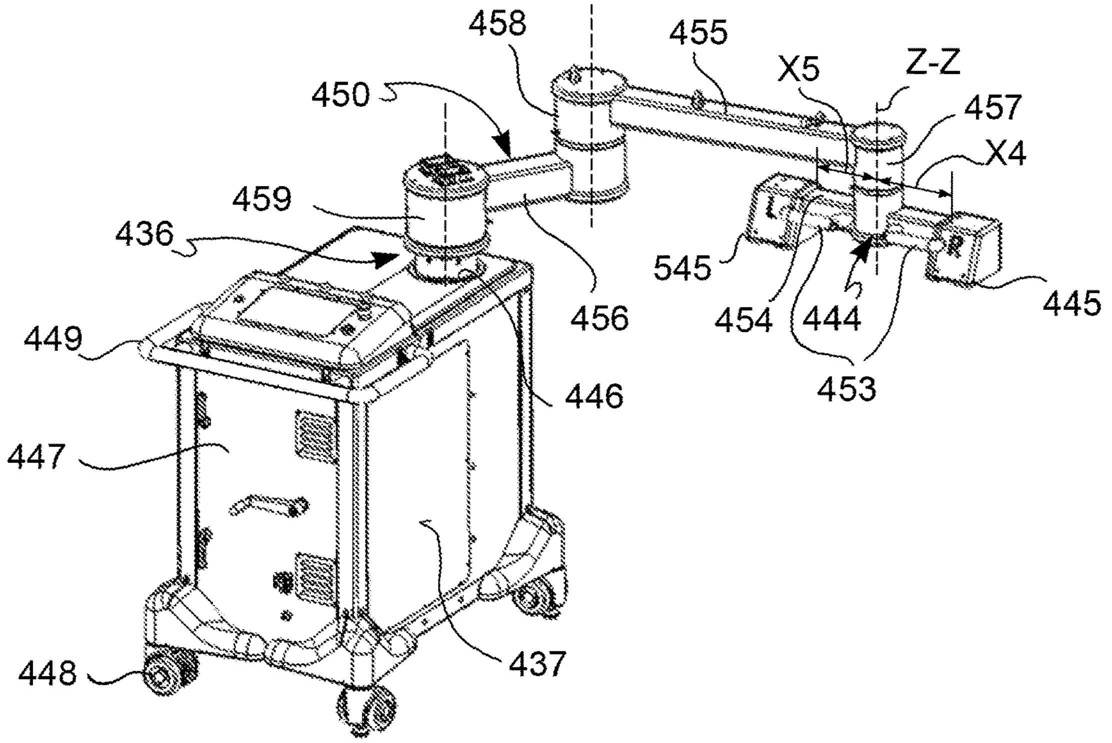
FIGS. 5 and 6 are axonometric views showing a robotic surgery assembly, according to an embodiment, in a the operative conditions of FIG. 3 and FIG. 4, respectively, wherein draping and cabling are not shown for sought of clarity.
Figure 6:
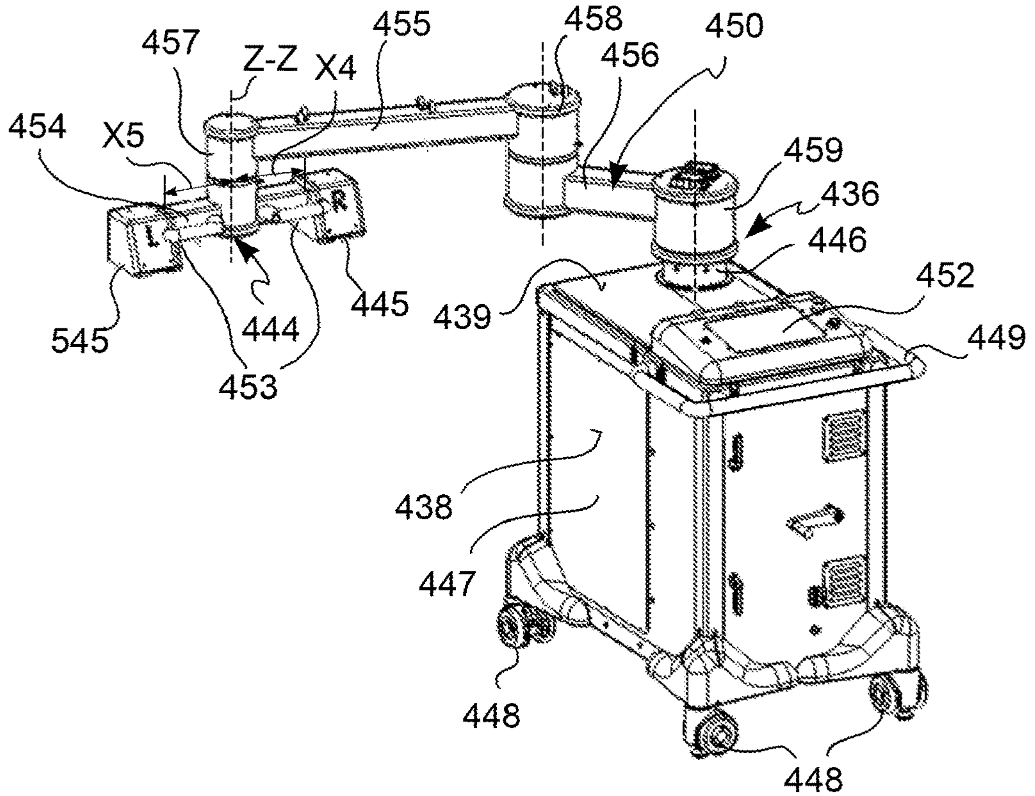
Figure 7:
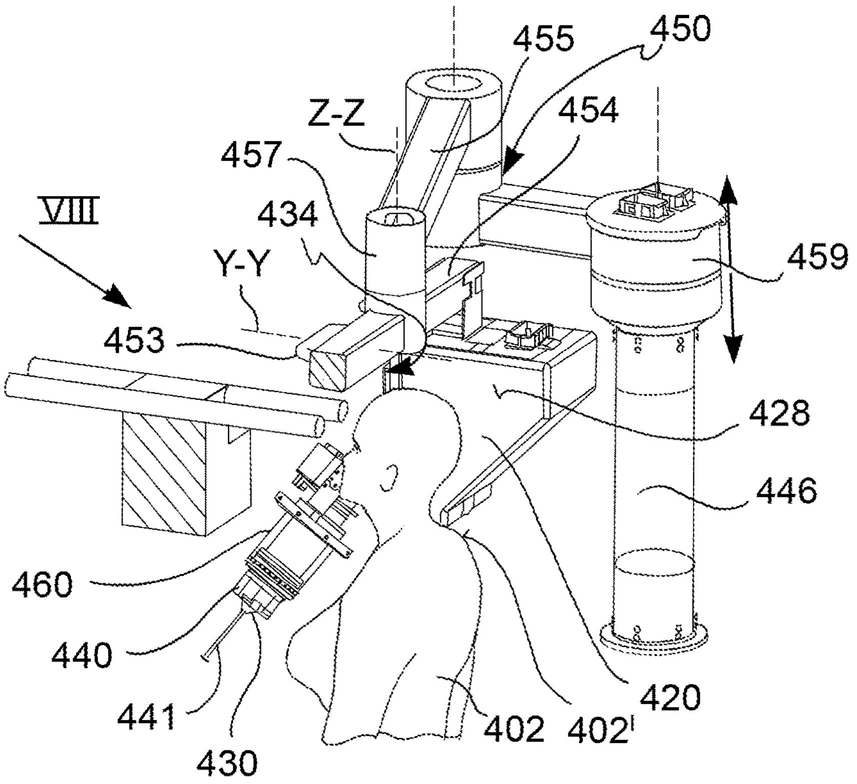
FIG. 7 is a cut-away axonometric view depicting a portion of a robotic surgery assembly, according to an embodiment, and a surgeon.
Figure 8:
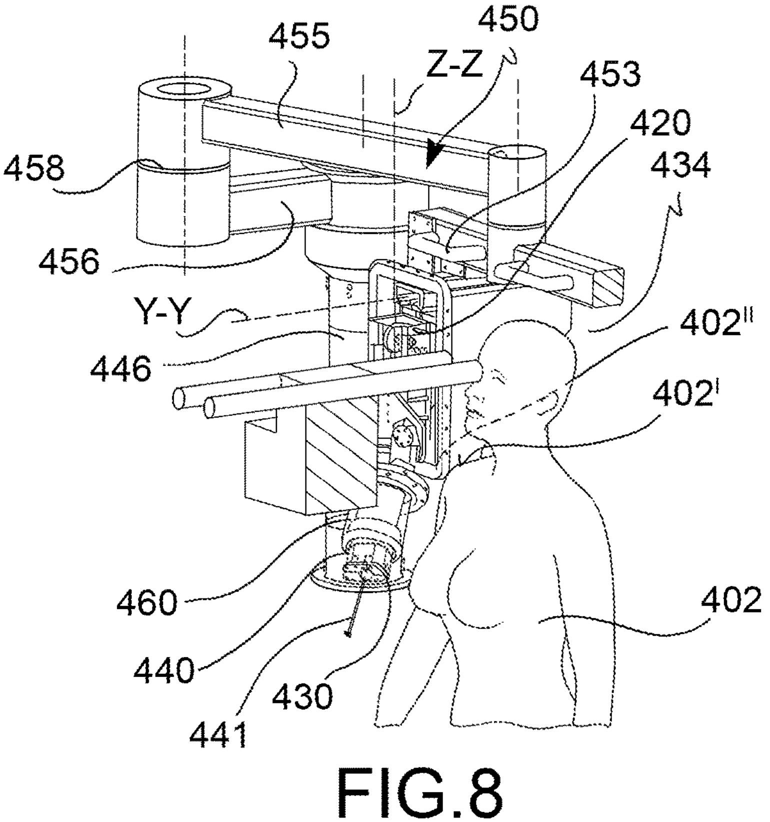
FIG. 8 is a cut-away axonometric view from the point of view indicated by arrow VIII of FIG. 7.

According to a general embodiment, it is provided a transmission component 410 for a robotic surgery assembly 401.

According to an embodiment, said transmission component is made of metal material.

According to an embodiment, in said robotic surgery assembly 401 is defined a proximal-distal direction W-W. According to an embodiment, said proximal-distal direction W-W is substantially coinciding with the direction of longitudinal development of the robotic surgery assembly 401. According to an embodiment, said proximal-distal direction W-W is substantially coinciding with the direction of longitudinal development of the robotic surgery assembly 401 is coincident with the direction of transmission of the forces between the passive macro-positioning arm and the sterile adapter, and preferably between the passive macro-positioning arm and the shaft of a surgical instrument distally attached to the sterile adapter. Those skilled in the art will appreciate that when the assembly 401 comprises a pair of motorized manipulators both connected to the same macro-positioning arm, a local proximal distal direction may be defined for each for each of the two branches, i.e. between each motorized manipulator and the respective sterile adapter, and preferably between each motorized manipulator and the shaft of a surgical instrument distally attached to the respective sterile adapter.

Said transmission component 410 comprises at least one first fixing portion 411, or proximal fixing portion 411, suitable to rigidly connect to a motorized manipulator 420, 520. According to an embodiment, said first fixing portion 411 comprises proximal fixing means 421, for example comprising at least one female element and/or at least one male element, directed locally along the proximal-distal direction W-W.

According to an embodiment, said transmission component 410 comprises at least one second fixing portion 412, or distal fixing portion 412, suitable to rigidly connect to a sterile adapter 430, 530. According to an embodiment, said second fixing portion 412 comprises distal fixing means 422, for example comprising at least one female element and/or at least one male element, directed locally along the local proximal-distal direction W-W.

For example, said fixing means 421 and/or 422 comprise threaded through holes suitable to receive threaded screws for connecting directly or indirectly, by interpostition of further transmission elements, respectively to said motorized manipulator 420, 520 and said sterile adapter 430, 530.

According to an embodiment, said local proximal-distal direction W-W coincides locally with the direction of transmission of the mechanical action from said motorized manipulator to said sterile adapter.

Said component 410 comprises a component body 415 between said first fixing portion 411 and said second fixing portion 412.

Said first fixing portion 411 and said second fixing portion 412 are held in respective mutual position by said component body 415. According to an embodiment, said component body 415 has a volumetric encumber comprising a body thickness 414. According to an embodiment, said body thickness 414 extends locally parallel the local proximal-distal direction W-W when in operative conditions [i.e. connected to the motorized manipulator 420, 520].

According to an embodiment, said component body 415 comprises at least a portion of a plate 413.

According to an embodiment, said plate 413 of said component body 415 comprises a first plate surface 416 suitable to face proximally and a second plate surface 417, opposite with respect to said first plate surface 416.

According to a preferred embodiment, said first fixing portion 411 and said second fixing portion 412 are distanced of an offset distance d1 one another. The offset distance d may be evaluated in respect of the vertical direction Z-Z, when in operative condition and depends on the orientation of the transmission component 410 in respect of the motorized manipulator 420, 520 upstream thereto. According to an embodiment, at least one edge 473 of the plate 413 is oriented parallel to said offset distance d.

The offset distance d may be evaluated in a direction orthogonal to the local proximal-distal direction W-W so that a manipulation action received from the motorized manipulator 420, 520 is transmitted shifted of said offset distance d1 to said sterile adapter 430, 530. Preferably, the manipulation action is a translation action directed along three mutually orthogonal directions X-X, Y-Y, Z-Z. Thereby the local proximal-distal direction W-W downstream the component 410 is offset of said offset distance d1 with respect to the local proximal-distal direction W-W upstream the component 410. In other words, the local proximal-distal direction W-W evaluated at said first fixing portion 411 is offset of said offset distance d1 with respect to the proximal-distal direction W-W evaluated at said second fixing portion 412. For the purpose of evaluation of said offset distance d, if the first fixing portion 411 and/or the second fixing portion 412 have a given global surface area A1 and/or A2, the respective fixing portion 411 and/or 412 is evaluated geometrical center G1 and/or G2 of said given global surface area A1 and/or A2.

According to an embodiment, the mutual orientation of the global surface area A1 of the first fixing portion 411 and the global surface area A2 of the second fixing portion 412 is angularly offset in at least one plane, for example in at least a horizontal plane and/or a vertical plant. Preferably, the mutual orientation of the global surface area A1 of the first fixing portion 411 and the global surface area A2 of the second fixing portion 412 is angularly offset in at least two planes [i.e. horizontal and vertical] so that to form a solid angle Ω.

According to an embodiment, said component body 415 comprises at least one rigidly locked joint 418 suitable for providing a first angular offset between the global surface area A1 of the first fixing portion 411 and the global surface area A2 of the second fixing portion 412. Thereby, the local proximal-distal direction W-W evaluated distally to said component 410 is oriented offset of said first angular offset with respect to said local proximal-distal direction W-W evaluated proximally to said component 410. According to an embodiment, the second fixing portion 412 is mounted on a bracket 419, 419', said bracket 419, 419' is in turn oriented offset of a second angular offset in respect of the first fixing portion 411. According to an embodiment the distance d2 between said bracket 419 and said first fixing portion 411 is greater than said offset distance d1.

According to an embodiment, said component body 415 comprises at least one bracket 419, 419' connecting said second surface 417 of the plate 413 to said second fixing portion 412. According to an embodiment, said at least one bracket 419, 419' comprises at least one rigidly locked joint 418, and said rigidly locked joint 418 is interposed between a first bracket portion 419 and a second bracket portion 419'. According to an embodiment, a distance d3 is defined between said second surface 417 and said joint 418 is According to an embodiment, said at least one second bracket portion 419' comprises said second fixing portion 412 and is preferably "L"-shaped. Thanks to the provision of a plurality of bracket portions 419, 419' integrally connected to a plate 413 through fixation means such as threaded connecting elements and the like, it is allowed to adjust the reciprocal position and orientation of the bracket portions 419, 419' and the plate 413 so that to adjust the mutual position and orientation of the first fixing portion 411 and the second fixing portion 412.

According to an embodiment, "rigidly locked joint 418" means that the rigidly locked joint is a rigid element devoid of relatively movable parts, and said rigid element devoid of relatively movable parts may be made in single piece. According to an embodiment, "rigidly locked joint 418" does not necessarily mean a robotic rotatational/prismatic joint which is blocked.

Figure 18:
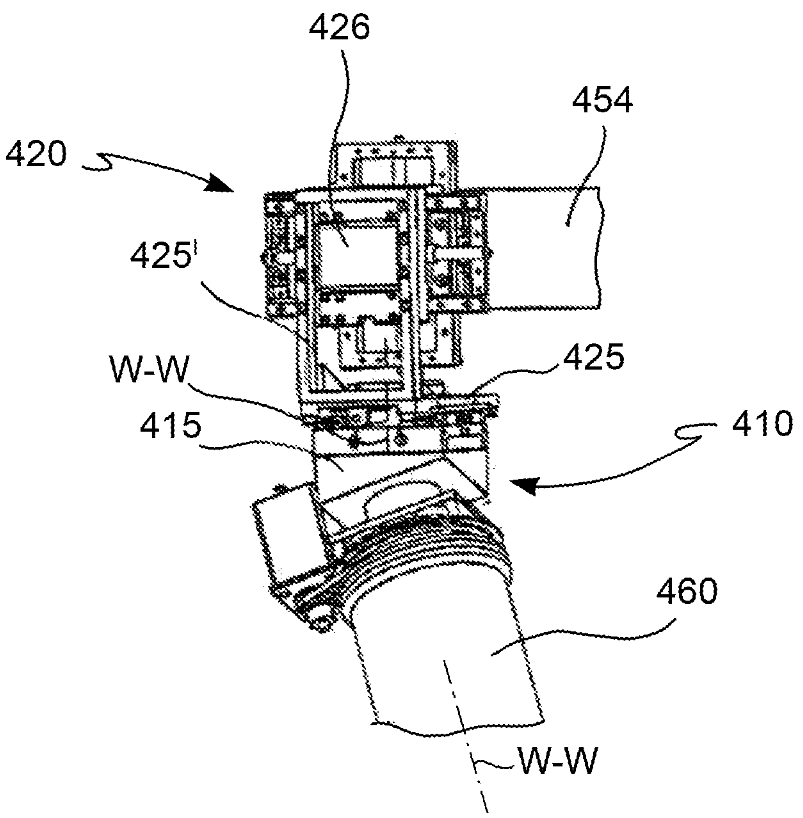
FIG. 18 is an axonometric view showing a transmission component for a robotic surgery assembly, according to an embodiment.
Figure 19:
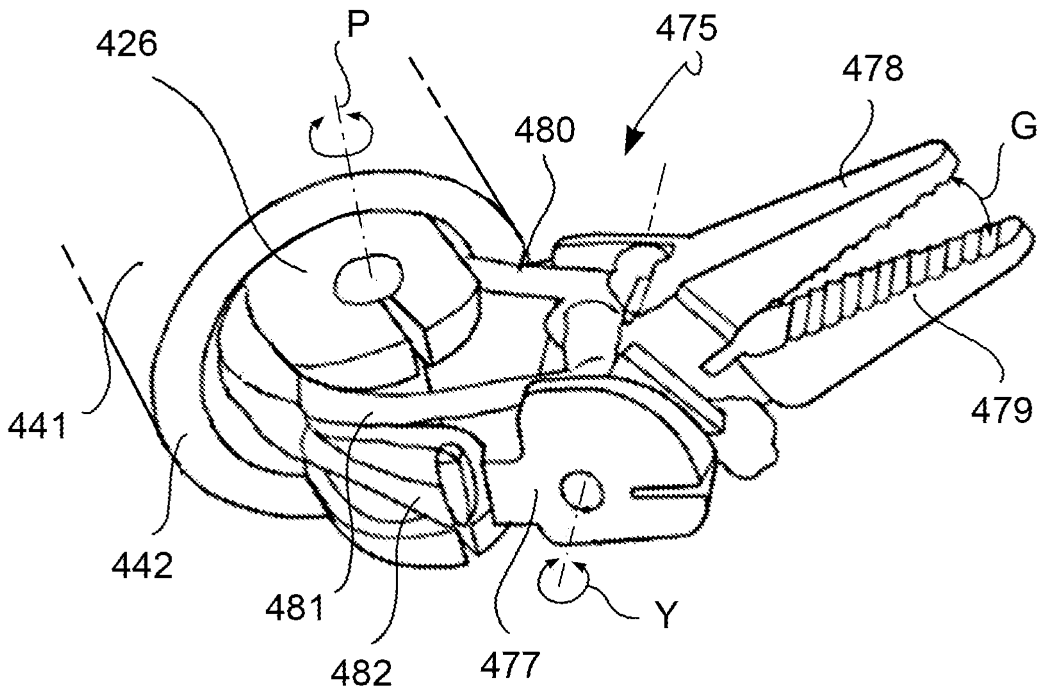
FIG. 19 is an axonometric view showing an articulated terminal tool at the distal end of a shaft, according to an embodiment.

According to an embodiment, said component body 415 is shaped as a convex solid element in single piece, as shown for example in FIG. 18.

According to a general embodiment, it is provided a robotic surgery assembly 401.

According to an embodiment, said robotic surgery assembly 401 comprises at least one transmission component 410 according to any one of the embodiments described above.

Said robotic surgery assembly 401 comprises at least one motorized manipulator 420, 520 comprising at least one motorized linear slider 423; 424; 425.

According to an embodiment, said at least one motorized linear slider 423, 424, 425 is suitable to slide in respect of a respective linear guide 423', 424', 425'.

According to an embodiment, said at least one motorized manipulator 420, 520 comprises three motorized linear siders 423, 424, 425, each of said motorized linear sliders is suitable for sliding along a direction X-X, Y-Y, Z-Z orthogonal to the direction of sliding of the other motorized linear sliders. Thereby, said motorized manipulator 420, 520 is a Cartesian motorized manipulator 420, 520. According to a preferred embodiment, said at least one motorized linear slider 423; 424; 425 comprises at least one vertical slider 425, suitable to slide along a substantially vertical direction Z-Z in respect of a vertical guide 425'. Thanks to the provision of a vertical linear slider 425 and two further sliders 423, 424 suitable for sliding along two mutually orthogonal horizontal directions X-X, Y-Y respectively, the gravity affects only the sliding of the vertical linear slider 425. Thereby, it is simplified the control of the motorized manipulators. Moreover, natural movements do not need to compose respective movements for each sliders, thus further simplifying the control.

According to an embodiment, said vertical linear slider 425 is associated to a counterweight 426 for compensate the gravitational acceleration having effect on said vertical linear slider 425.

According to an embodiment, said vertical linear slider 425 is the most distal slider among said at least one, and preferably three, motorized linear sliders 423, 424, 425.

According to an embodiment, said Cartesian motorized manipulator 420, 520 comprises a first horizontal linear guide 424' and a first horizontal motorized linear slider 424 suitable for sliding along a first horizontal direction Y-Y in respect of said first horizontal linear guide 424'; said first horizontal motorized linear slider 424 is integral with a second horizontal linear guide 423'; and said Cartesian motorized manipulator 420, 520 comprises a second horizontal motorized linear slider 423 suitable for sliding along a second horizontal direction X-X in respect of said second horizontal linear guide 423'; and said second horizontal motorized linear slider 423 is integral with said vertical guide 425'; and said vertical motorized slider 425 is suitable for sliding along the vertical direction Z-Z in respect of said vertical guide 425'.

According to an embodiment, the one or more motorized linear sliders 423; 424; 425 of a first motorized manipulator 420 of said pair of motorized manipulators 420, 520 are parallel to the one or more motorized linear slider 423; 424; 425 of a second motorized manipulator 520 of said pair of motorized manipulators 420, 520.

Preferably, both said motorized manipulators 420, 520 are attached to a same link 454 of a macro-positioning passive arm 450.

Thanks to the provision of said transmission component 410 fixed through said first fixing portion 411 to said vertical motorized slider 425 it is allowed to at least translate the manipulation action applied by said motorized manipulator 420, 520 in the horizontal direction X-X of said offset distance d1.

According to an embodiment, said robotic surgery assembly 401 further comprises at least one sterile adapter 430, 530, comprising a coupling device 433 suitable for connecting to a surgical instrument 440, 540. According to an embodiment, said sterile adapter 430, 530 forms together with a surgical drape 431 a draping assembly 432 suitable for impede mutual contamination between the part of the robotic surgery assembly 401 proximal to the sterile adapter 430, 530 and the surgical instrument 440, 540.

According to an embodiment, a local proximal-distal direction is defined W-W and the word "upstream" is meant equivalent as "proximally" and the word "downstream" is meant equivalent to the word "distally".

According to an embodiment, said transmission component 410 is interposed directly or indirectly between said at least one motorized manipulator 420, 520 and at least one sterile adapter 430, 530. Thereby, said transmission component 410 rigidly determine the relative mutual position and/or orientation of said at least one motorized linear slider 423, 424, 425, and preferably of said motorized vertical linear slider 425, of the motorized manipulator 420, 520 and said coupling device 433 of the sterile adapter 430, 530.

According to a preferred embodiment, a motor box assembly 460 is interposed between said transmission component 410 and said sterile adapter 430, 530. Thereby, said transmission component 410 rigidly determines the relative mutual position and/or orientation of said at least one motorized linear slider 423, 424, 425 of the motorized manipulator 420, 520 and said motor box assembly 460. According to a preferred embodiment, said vertical motorized slider 425 comprises a distal fixing portion of vertical slider 435 connected to said proximal fixing portion 411 of said transmission component. Thereby, the transmission component 410 connects said vertical motorized slider 425 to said motor box assembly 460.

According to an embodiment, said robotic surgery assembly 401 comprises at least one surgical instrument 440, 540 connectable to said coupling device 433 of the sterile adapter 430, 530. According to an embodiment, said at least one surgical instrument 440, 540 is detachably connectable to said sterile adapter 430, 530. According to an embodiment, said at least one surgical instrument 440, 540 comprises a shaft 441, 541, and said shaft 441, 541 extends preferably locally along the local proximal-distal direction W-W.

Thereby, said shaft 441, 541 is offset in respect of the sliding direction X-X, Y-Y, Z-Z of said at least one motorized linear slider 423, 424, 425. According to an embodiment, said shaft 441, 541 is offset in respect of each and all the sliding directions X-X, Y-Y, Z-Z of said three motorized linear sliders 423, 424, 425.

According to an embodiment, said motor box assembly 460 comprises at least one actuator suitable for actuating at least one respective degree of freedom of said surgical instrument 440, 540 in respect of said sterile adapter 430, 530. According to an embodiment, said motor box assembly 460 comprises a roll motor 461 and a roll actuator, for example comprising a transmission belt 462, suitable for pivoting said surgical instrument 440, 540 comprising said shaft 441, 541 about the axis of longitudinal development of the shaft 441, 541, and preferably about the local proximal-distal direction W-W. According to an embodiment, said motor box assembly 460 comprises a roll motor 461 and a roll actuator 462 suitable for pivoting said sterile adapter 430, 530 about the local proximal-distal direction W-W and preferably about the axis of the longitudinal development of the shaft 441, 541. Preferably, said surgical instrument 440, 540 is integral with said sterile adapter 430, 530 when the surgical instrument 440, 540 is connected to said sterile adapter 430, 530. Thereby, the roll motor 461 is upstream in respect to said draping assembly 432.

According to a preferred embodiment, said robotic surgery assembly 401 comprises two motorized manipulators 420, 520 forming a pair of motorized manipulators 420, 520. Thereby, said robotic surgery assembly 401 comprises a first motorized manipulator 420 and a second motorized manipulator 520. According to an embodiment, each motorized manipulator 420, 520 comprises a case 427, 527 individually encasing each of said at least two motorized manipulators 420, 520. Thereby, said robotic surgery assembly 401 comprises two cases 427, 527, namely a first case 427 and a second case 527.

According to a preferred embodiment, both said two motorized manipulators 420, 520 are fixed a macro-positioning arm 450 at substantially the same height so that said two motorized manipulators 420, 520 flanks one another in the horizontal direction X-X. According to an embodiment, each motorized manipulator 420, 520 comprises a fixing portion 451, for example a fixing bracket, for fixation to said macro-positioning arm 450. According to an embodiment, said fixing portion 451 is integral with one of said linear guides 423', 424', 425', and preferably to an horizontal linear guide 423', 424', and more preferably to said second horizontal linear guide 424'.

According to a preferred embodiment, each of said cases 427, 527 encases at least one of said transmission component 410. According to an embodiment, said each case 427, 527 comprises a proximal case portion 428, 528 and a distal case portion 429, 529, distal in respect of said proximal case portion 428, 528, wherein said proximal case portion 428, 528 encases a respective motorized manipulator 430, 530, and wherein said distal case portion 429, 529 encases a respective transmission component 410.

The provision said transmission components 410 downstream to the motorized manipulators 420, 520, respectively makes the two shafts 441, 541 of the surgical instruments 440, 540 converging one towards the other. Thereby, the distal end 442, 542 of each shaft 441, 541 reaches a same shared working volume 404. An articulated terminal tool 475, for example an end effector, may be provided at the distal end of each shaft 441, 541, such as a wrist for robotic surgery having a tip portion suitable for performing surgery on a patient. According to an embodiment, said articulated terminal tool 475 provided at the distal end of each shaft 441, 541 has one or more degrees of freedom P,Y,G, preferably at least one pitch P degree of freedom, at least one yaw Y degree of freedom and at least one grip G degree of freedom. According to an embodiment, said articulated terminal tool 475 comprises a plurality of links 476, 477, 478, 479 articulated one another and a plurality of actuation cables 480,481,482 of actuating the degrees of freedom P,Y,G of the links 476, 477, 478, 479 of the articulated terminal tool 475. Each link 476, 477, 478, 479 is preferably made in single piece by means of wire electro-discharge machining. The actuation cables 480,481,482 slide onto convex external surfaces of said links 476, 477, 478, 479.

According to an embodiment, each case 427, 527 is as tight-fit as possible to the respective motorized manipulator 420, 520 and transmission component 401 and forms a elbow between the respective proximal case portion 428, 528 and distal case portion 429, 529. Thereby, the two cases 427, 527 have a concave portion [i.e. the elbow] facing one another so that the shafts 441, 541 of the surgical instruments 440, 540 attached distally thereto converge one towards the other both reaching said shared working volume 404 with a distal end 442, 542 thereof.

According to an embodiment, a distal end 442 of a first shaft 441 reaches a first working volume 403 and a distal end 542 of a second shaft 541 reaches a second working volume 503, wherein said first working volume 403 and said second working volume 503 are co-penetrated defining said shared working volume 404, said shared working volume 404 can be reached by both distal portions 442, 542 of each shaft 441, 541 for any operative position of the sliders 523, 524, 525. In other words, the shared working volume 404 is given by the volume of intersection of the first working volume 403 and the second working volume 503.

Thanks to the provision of said sliders, each working volume 403, 503 is parallel to the directions of sliding X-X, Y-Y, Z-Z of the sliders 423, 424, 425 of the respective motorized manipulator 420, 520. Thanks to the provision of said vertical slider 425 and said horizontal sliders 423, 424, the same shared working volume 404 is a horizontal parallelepiped. The word “parallelepiped” used herein encompasses also the case wherein the same shared working volume 404 is a cube.

Preferably, said same shared working volume 404 is at least the 50% of each one of said first and second working volumes 403, 503, and preferably is at least the two thirds of each one of said first and second working volumes 403, 503, and more preferably is substantially the 90%. According to an embodiment, said first and second working volumes 403, 503 are completely co-penetrated forming a single shared working volume 404.

Thanks to such a robotic surgery system, both the distal ends of the shafts 441, 541 reach a shared working volume and are able to move within said shared working volume parallel one another.

The operator, for example a surgeon controlling the slave robotic surgery assembly from a master console, can thereby feel when one or both the shaft has reached the boundary of the shared working volume. In this way, the comfort for the surgeon in enhanced.

According to a preferred embodiment, said cases 427, 527 are distanced one another in an horizontal direction X-X, Y-Y, and preferably along said first horizontal direction X-X, of a predefined horizontal distance X2. According to a preferred embodiment, said predefined horizontal distance X2 is greater than said offset distance d1. According to a preferred embodiment, said predefined horizontal distance X2 is greater than twice said offset distance d1.

The predefined horizontal distance X2 may vary along the local proximal-distal direction W-W. According to a preferred embodiment, said predefined horizontal distance X2 is greater at the proximal case portions 428, 528 encasing the respective motorized manipulator 430, 530 than at the distal case portions 429, 529 encasing the respective transmission component 410. Thereby the predefined horizontal distance X2 preferably decreases moving downstream towards the sterile adapter.

Advantageously, a window 434 or passage 434 is delimited at least partially by said two cases 427, 527. Preferably, said window 434 is delimited by said two cases 427, 527 in the first horizontal direction X-X. The provision of said window 434 forms a through passage along the second horizontal direction Y-Y between said two motorized manipulators 420, 520. Thanks to said window 434 a volume, which may be left free, is provided between the cases 427, 527 encasing said motorized manipulators 420, 520. The window 434 is preferably as wide as the predefined horizontal distance X2 in the first horizontal direction X-X.

Thanks to the reciprocal position and orientation of the two motorized manipulators 420, 520 encased within said respective cases 427, 527 delimiting said window 434, a surgeon 402 can occupy a position behind said window 434 so that the manipulators 420, 520 results positioned above the surgeon's 402 shoulders 402'.

According to an embodiment, said robotic surgery assembly 401 is associated to a microscope assembly 470 comprising an image acquisition portion 471 connected to a vision device 472 suitable for providing the surgeon with a magnified image of the shared working volume 404. The vision device 472 preferably comprises at least one ocular and preferably a pair of oculars. According to a preferred embodiment, said image acquisition portion 471 is an optical microscope for microsurgery. A microscope drape may be provided to drape at least the oculars of the vision device 472.

Figure 9:
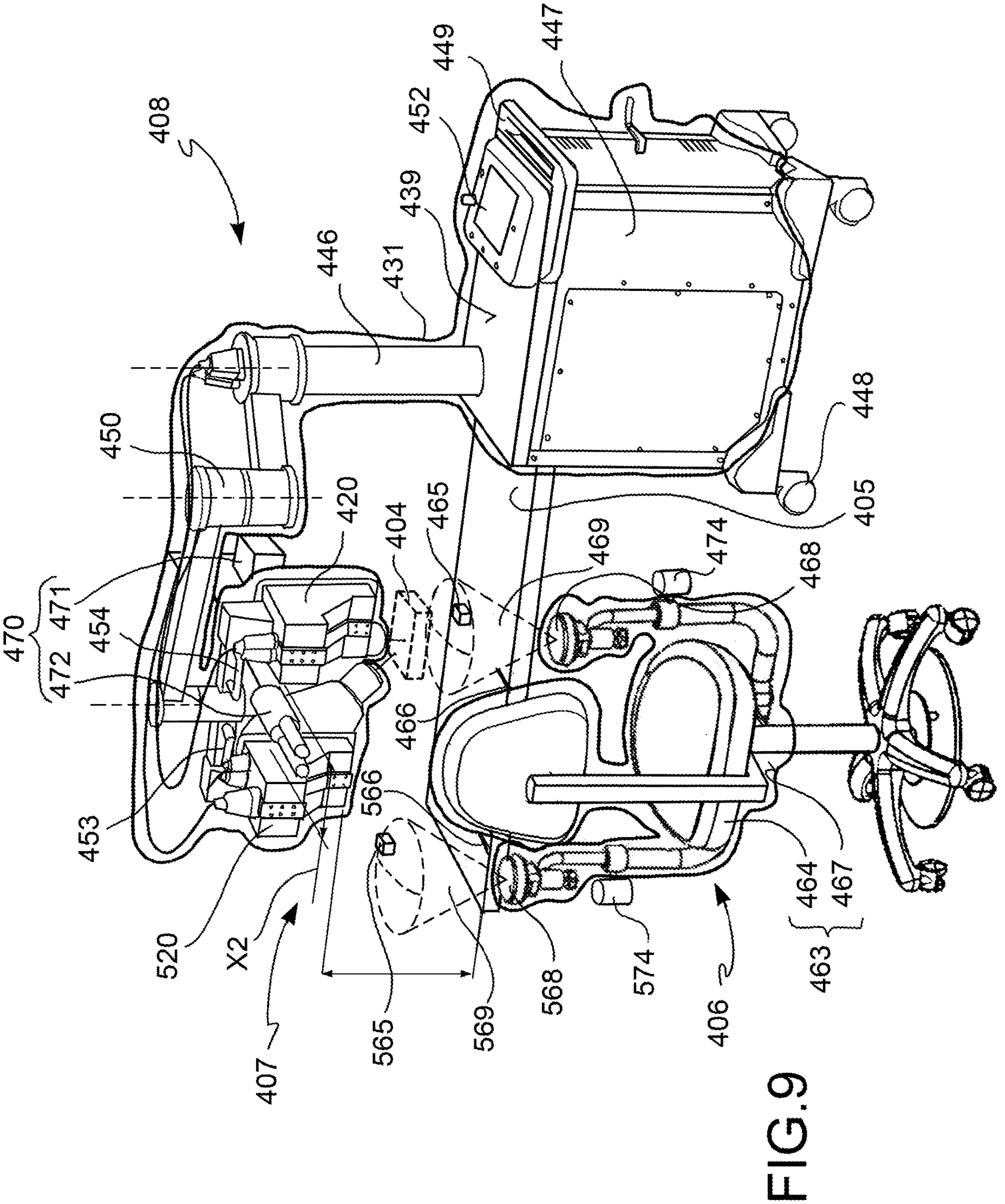
FIG. 9 is a sketch showing as axonometric view an operating arena comprising a robotic surgery assembly, according to an embodiment, a microscope assembly, and an operatory table.
Figure 11:
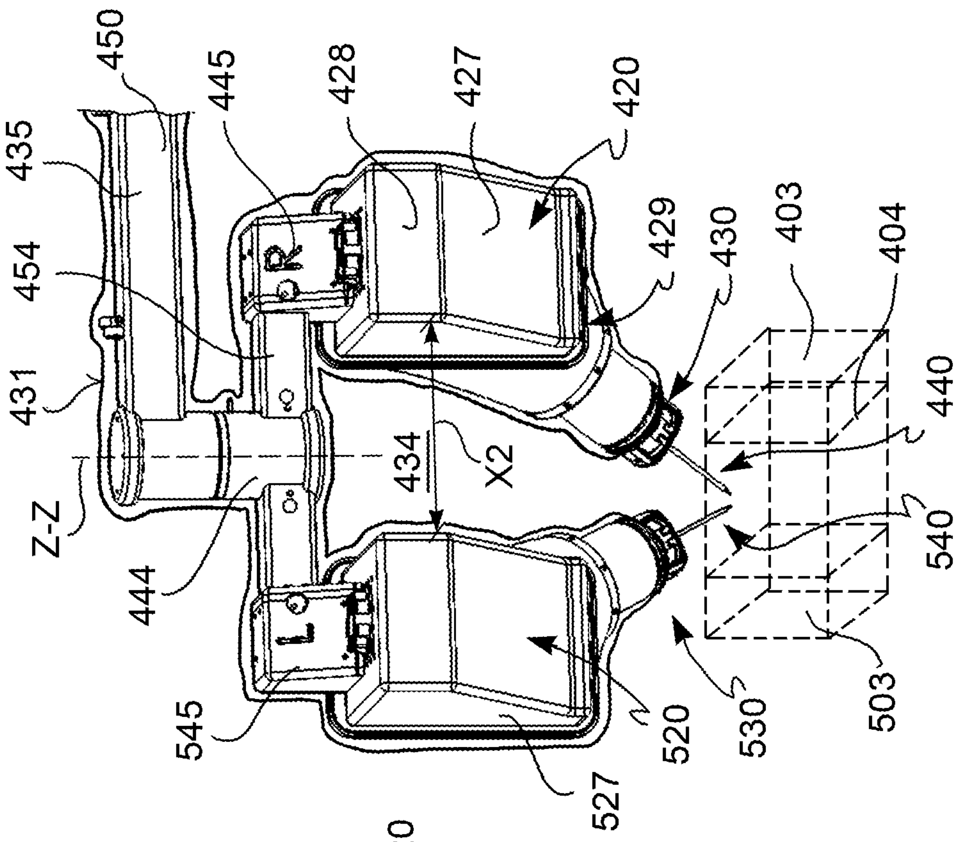
FIG. 11 is a back axonometric view of a portion of the robotic surgery assembly shown in FIG. 10.
Figure 10:
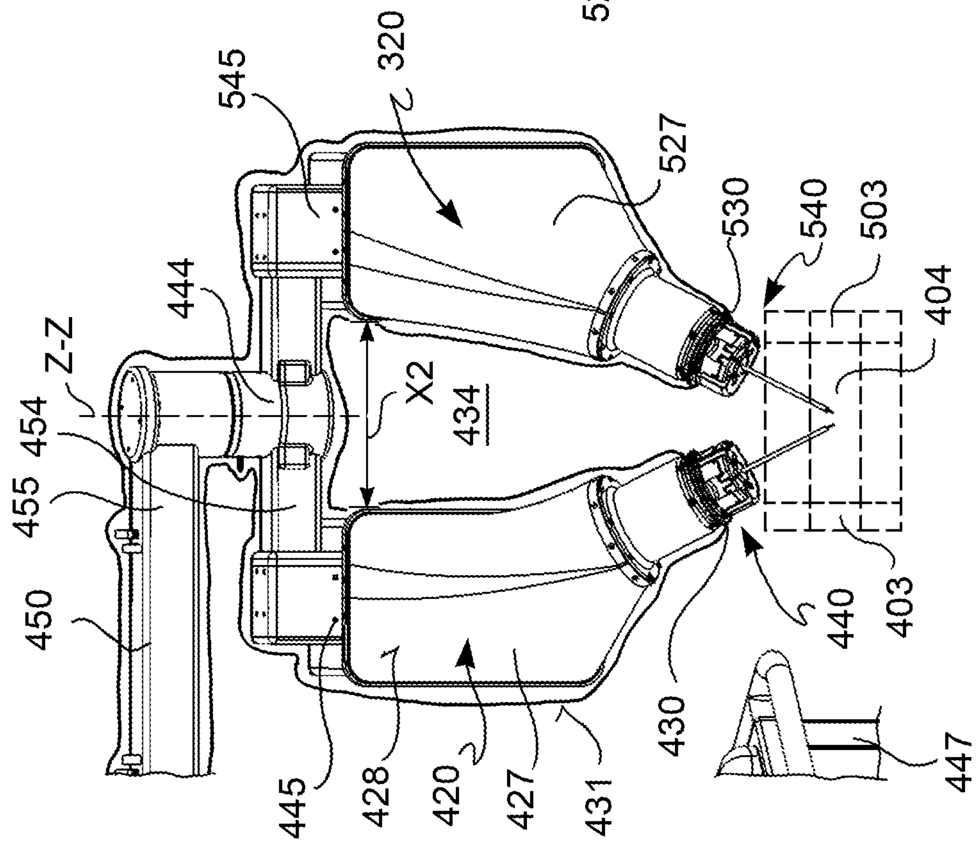
FIG. 10 is a front axonometric view of a portion of a robotic surgery assembly, according to an embodiment.
Figure 13:
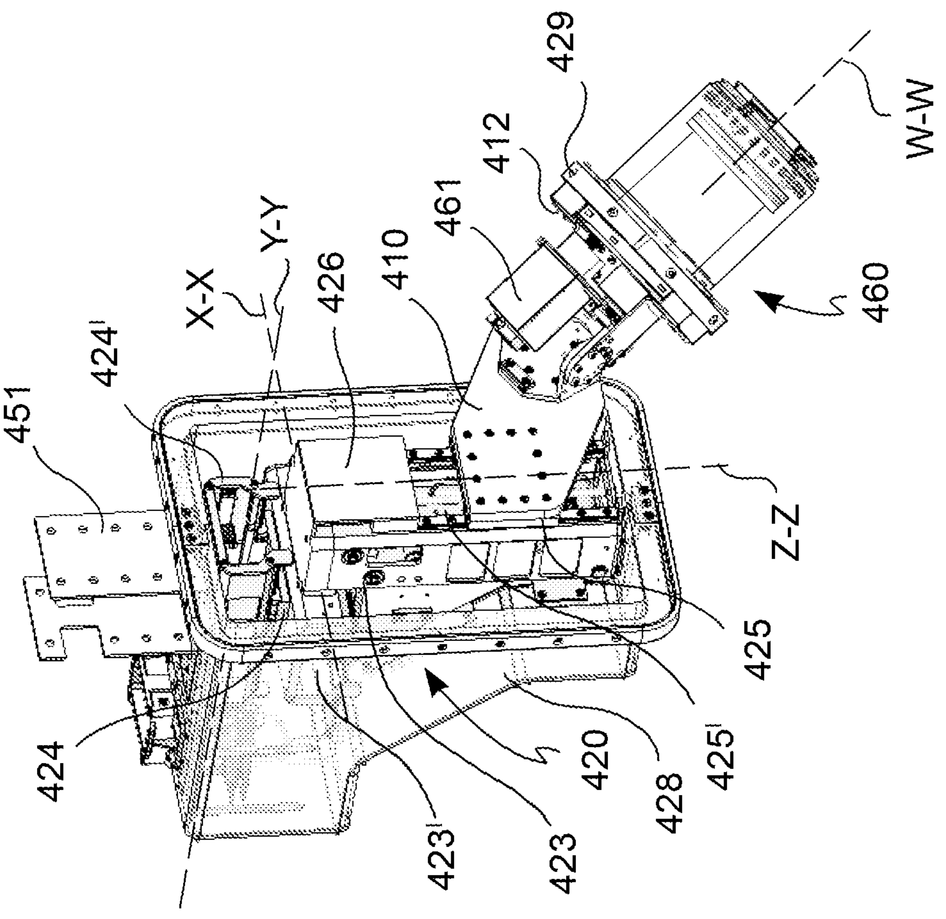
FIGS. 12, 13 and 14 are axonometric views of a portion of a robotic surgery system, according to an embodiment, wherein some parts are transparent for sought of clarity.
Figure 12:
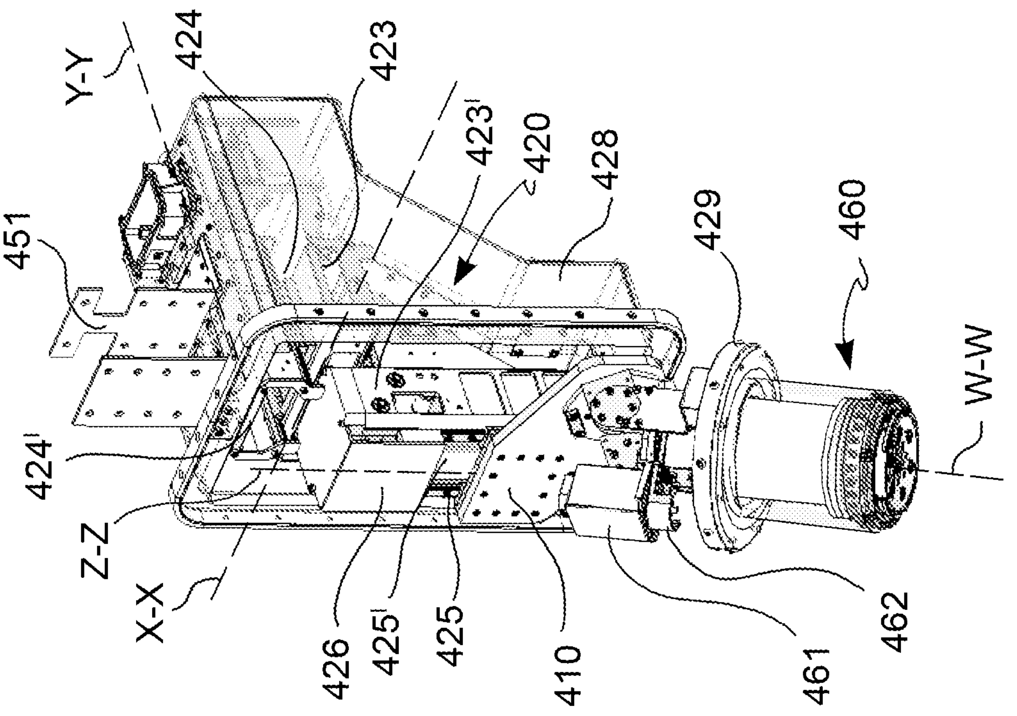
Figure 15:
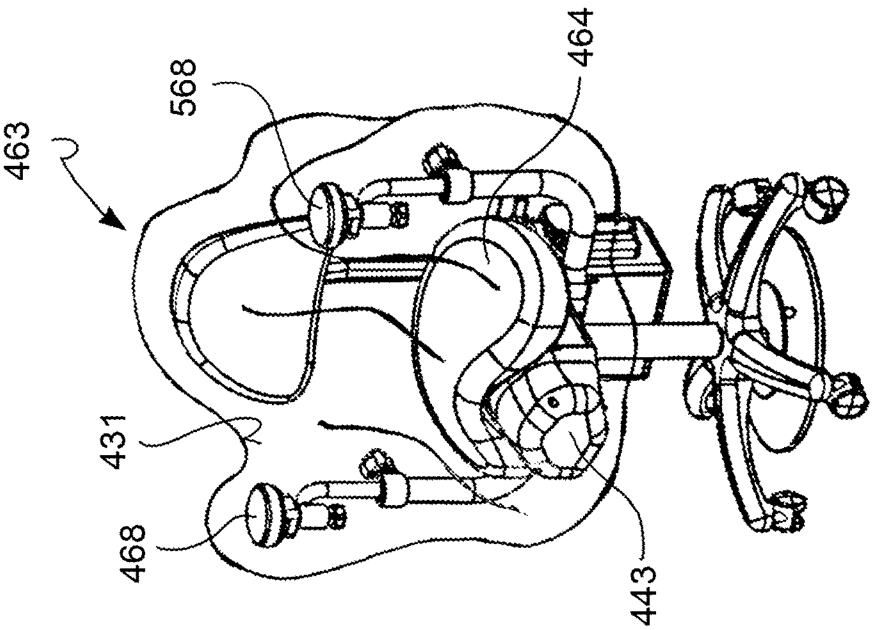
FIG. 15 is an axonometric view of a sterile console, according to an embodiment.
Figure 14:
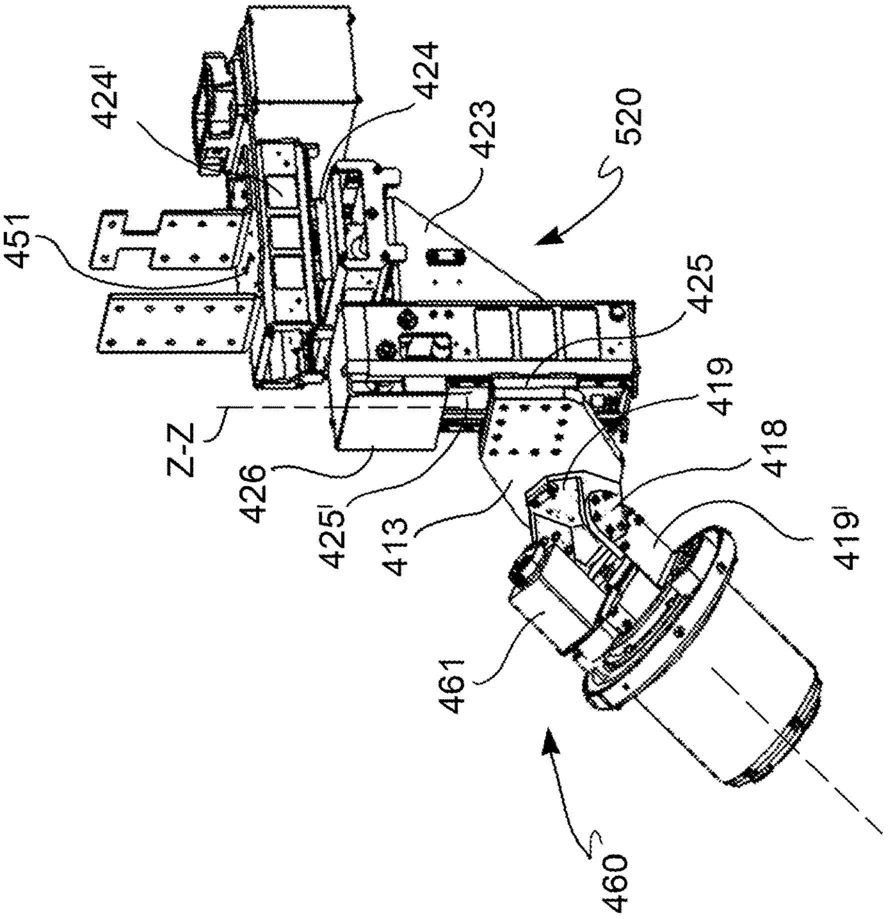
Figure 16:
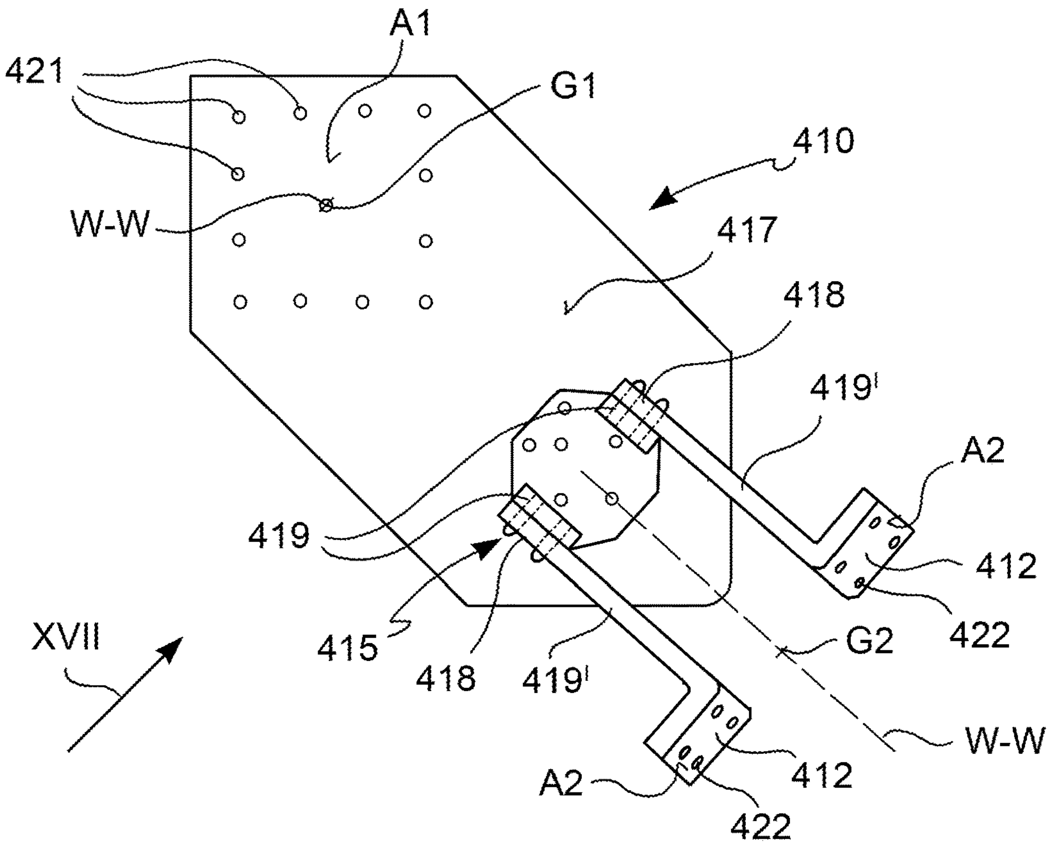
FIG. 16 is a plane view of a transmission component for a robotic surgery assembly, according to an embodiment.
Figure 17:
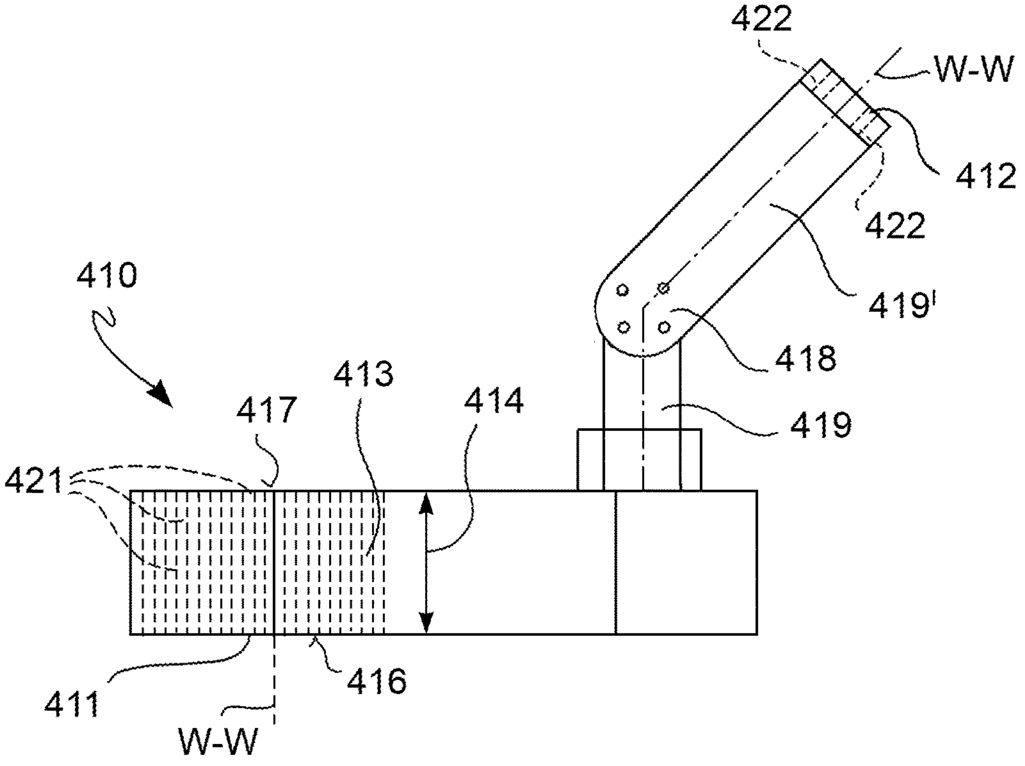
FIG. 17 is a view according to the direction indicated by arrow XVII of FIG. 16.

According to a preferred embodiment as shown for example in FIG. 9, said at least one ocular 472 of the microscope assembly 470 are at least partially within said window 434. Thereby said at least one ocular 472 is between said cases 427, 527.

Thanks to the provision of said transmission component 410 within each case 427, 527 it is also provided an angular offset along the second horizontal direction Y-Y so that the shafts 441, 541 of the surgical instruments 440, 540 converges towards each other pointing with the distal ends 442, 542 thereof to a position forwarded in respect to the vertical slider 425 along the second horizontal direction Y-Y. Thereby, the shared working volume 404 lies on or above an operatory table 405 located forwarded in respect to the surgeon 402. Thereby the surgeon 402 can alternate robotic-aided microsurgery looking at the oculars 472 and traditional hand microsurgery looking directly downwards at the patient anatomy on said operatory table 405. When a surgeon 402 face the window 434 in operative conditions, the second horizontal direction Y-Y is substantially parallel to the sagittal plane of the surgeon 402.

Thanks to the provision of said transmission component 410 within each case 427, 527 as described above the oculars 427, 527 result above the surgical instruments 440, 540, the surgical instruments 440, 540 in turn are above the operating table 405. The surgeon 402 approaches the operatory table frontally [i.e. along the second horizontal direction Y-Y]. The shafts 441, 541 of the surgical instruments 440, 540 both approach with distal ends 442, 542 thereof the shared working volume 404 frontally [i.e. along the second horizontal direction Y-Y] and from above [i.e. along the vertical direction Z-Z] and converging towards each other in the first horizontal direction X-X [i.e laterally]. Thereby, the volumetric encumber of the robotic surgery system 401 allows the surgeon 402 to see the shared working volume 404 and the relevant portion of the patient's anatomy with his eyes 402" with and without the oculars 472 of the microscope assembly 470 by simply directing his/her eyesight. In other words, the volumetric encumber of the robotic surgery system 401, thanks to the transmission components 401 encased within said cases 427, 527, avoids to hide the working volume 404 from the surgeon's eyesight.

According to an embodiment, said robotic surgery system 401 comprises a macro-positioning arm 450.

Preferably, said macro-positioning arm 450 can be passively moved and do not require motors for its positioning. Thereby the macro-positioning arm 450 comprises at least one handle 453 for the hand manipulation of the macro-positioning arm 450 by an operator, for example a surgeon 402 and/or a member of the surgical équipe. Dynamic brakes may be provided within the rotational joints to dampen the displacement of the macro-positioning arm 450.

According to an embodiment, said macro-positioning arm 450 comprises a plurality of arm links 454, 455, 456 connected one another in series and articulated through rotational joints 457, 458, 459. Thereby, said macro-positioning arm 450 comprises a most distal link 454, or first link 454, having an elongated distal link body oriented substantially horizontally and connected proximally to a second link 455 through a distal rotational joint 457. Preferably, said distal rotational joint 457 is connects substantially to a central portion 444 of the distal link 454 so that the distal link 454 may pivot around the distal rotational joint 457. Preferably, the central portion 444 is at half the length of the distal link 454 According to a preferred embodiment, the axis of the distal rotational joint 457 is oriented vertically.

According to an embodiment, said macro-positioning arm 450 comprises said distal link 454 connected to said pair of motorized manipulators 420, 520, proximally to said distal link 454 comprises a second link 455 connected to said distal link 454 through said distal rotational joint 457 having rotational axis substantially vertical, and proximally to said second link 455 comprises a third link 456 connected to said secondo link through a second rotational joint 458 having rotational axis substantially vertical, and wherein said second link 455 is oriented horizontally and extends above both to said distal link 454 and said first link 456 so that the distal link 454 and the first link 456 are at substantially the same height. According to a preferred embodiment, said third link 456 is connected through a third rotational joint 459 to a telescopically extendable portion 446, suitable to extend in the vertical direction Y-Y to adjust the height of the macro-positioning arm 450 in respect to the operatory table 405 and to the surgeon 402, the robotic surgery assembly 401 further comprising a robotic cart 447 or tower 447 and said telescopically extendable portion 446 is extendable in respect to said cart 447. According to an embodiment, said cart 447 comprises ground contact units 448, such as wheels 448. At least one surgical drape 431 may be provided to drape the macro-positioning arm 450 and at least a portion of the cart 447. The cart 447 may comprises at least one cart handle 449 for moving the cart 447 within around the operatory bed 405. According to an embodiment, said macro-positioning arm 450 is connected to said robotic cart 447.

According to an embodiment, said distal link 454 further comprises two attachment portions 445, 545 each suitable to connect to one motorized manipulator 420, 520, and preferably to the fixing portion 451 of the respective motorized manipulator 430, 530, the distal rotational joint 457 is between the attachment portions 445, 545 of the distal link 454 so that a pivoting action P4 pivoting the distal link 454 about the distal rotational joint 457 of a pivoting angle, for example a pivoting angle measuring substantially 180 degrees or half turn, determines the motorized manipulators 420, 520 to flip their position, for example in respect to the second link 455 of the macro-positioning arm 450, and/or in respect to the cart 477, and/or in in respect to the surgeon 402, and/or the operatory table 405.

According to a preferred embodiment, the position of the attachment portions 445, 545 of the distal link 454 are symmetrically arranged in respect to the distal rotational joint 457. In other words, a first distance X4 between the rotation axis of the distal rotational joint 457, which is preferably vertical, and the first attachment portion 445 connecting to the first motorized manipulator 420, 520 is equal to a second distance X5 between the rotation axis of the distal rotational joint 457 and the second attachment portion 545. Thereby the dynamic and static balance of the robotic elements downstream the macro-positioning arm 450 is enhanced improving the stability thereof in operative conditions.

According to a preferred embodiment, the distal link 454 and the motorized manipulators 420, 520 encased within the respective cases 427, 527 delimit together said window 434 upwardly and laterally. According to a preferred embodiment, the distal link 454 and the motorized manipulators 420, 520 encased within the respective cases 427, 527 form a "reversed-U" shaped structure delimiting partially said window 434. In other words, the distal link 454 and the motorized manipulators 420, 520 encased within the respective cases 427, 527 form a horseshoe shaped structure delimiting partially said window 434. According to an embodiment, both said at least two motorized manipulators 420, 520 are attached to a same link 454 of the macro-positioning passive arm 450.

According to an embodiment, the robotic cart 447 comprises a first side 437 and a second side 438, the first side 437 and the second side 438 are opposite one another in a horizontal direction in respect to said telescopically extendable portion 446, and preferably are opposite one another in said first horizontal direction X-X. The combined provision of said macro-positioning arm 450 having said plurality of rotational joints 457, 458, 459 connecting and articulating said plurality of links 454, 455, 456, wherein said distal link 454 is connected in its central portion 444 to the second link 455, and the robotic cart 477 having said opposite sides 437, 438, allows to position the shared working volume 404 facing either said first side 437 or said second side 438, thereby improving the versatility of the robotic surgery assembly 401. Thereby, the robotic cart 477 can be placed substantially in any position in respect to the operatory bed 405. Thereby the surgeon 402 can face said window 434 and access the patient's anatomy through said window 434 in any mutual position of the robotic cart 477 and the operatory bed, while the distal ends 442, 542 of the shafts 441, 541 of the surgical instruments 440, 540 always approach the operatory bed 405 frontally and the manipulators 420, 520 are in the same horizontal position in respect to the surgeon 402.

According to an embodiment, the cart 477 comprises a top portion 439 having a polygonal shape and defining a top portion perimeter 435 forming a plurality of corner portions 436, and wherein said macro-positioning arm 450 is connected to one of said corner portions 436. The top portion 439 of the cart 477 may comprise a screen 452 to display information on the state of the robotic surgery assembly 401.

According to an embodiment, said robotic surgery assembly 401 comprises a robotic slave portion 407 formed by said at least one surgical instruments 440, 540, said motorized manipulators 420, 520, and said at least one motor box assembly 460. According to an embodiment, said robotic surgery assembly 401 comprises a master controller assembly 406 comprising at least one master input tool 465, 565 suitable to detect a manual command and suitable to activate said salve part of the robot 407, for example to activate said at least one of said surgical instruments 440, 540 and/or at least one of said motorized manipulators 420, 520. For example, the position and orientation of said at least one master input tool 465, 565 is tracked by an electromagnetic and/or an optical tracking device comprising a field generator 443 generating a field, with the purpose of detecting at least the position and preferably also the orientation of the master input tool 465, 565 within said field for transmitting control signals to said slave part of the robot 407.

According to an embodiment, said master controller assembly 406 further comprises a sterile console 463 comprising a surgical chair 464 and a master drape assembly 467 draping the surgical chair 434 and preferably also draping said at least one master input tool 465, 565. According to an embodiment, said surgical chair 464 comprises at least one resting element 468, 568, for example dome shaped, for the surgeon 402 to rest his/her elbow thereon during surgery so that to define a cone of freedom of movement 469, 569 for the master input tool 465, 565 when grasped by the surgeon's hand. A dropping holster 474, 574 may also be provided at the master controller assembly 406 for the surgeon 402 to drop the at least one master input tool 465, 565 with the purpose of promote alternation of hand microsurgery and robotic-aided microsurgery. Hand surgery tools 466, 566 may also be provided for at the master console assembly 406 to promote the surgeon 402 to alternate hand microsurgery and robotic-aided microsurgery.

Preferably two master input tools 465, 565 are provided, each master input tool controlling one branch of the robotic system, each branch comprising one of said motorized manipulators and the elements downstream attached thereto.

According to a general embodiment, a operatory arena 408 comprises at least one robotic surgery assembly 401 according to any one of the embodiments described above, and an operatory table 405 according to any one of the embodiments described above, and a microscope assembly 470 according to any one of the embodiments described above. As those skilled in art will appreciate, "operatory table" means any location supporting the patient during surgery.

According to an embodiment, said operatory arena 408 comprises and a master controller assembly 406 according to any one of the embodiments described above. Preferably two master input tool are provided, each master input tool controlling one branch of the robotic system, each branch comprising one of said motorized manipulators and the elements downstream attached thereto.

According to a general operating mode, a method of repositioning of a slave robotic part 407 of a robotic surgery assembly 401 within an operatory arena 408 according to any one of the embodiments described above comprises the following steps.

The method comprises the step of exerting a pivoting action P4 pivoting the distal link 454 about the distal rotational joint 457 of a pivoting angle, so that the motorized manipulators 420, 520 flip their position in respect to a second link 455 of the macro-positioning arm 450.

According to a possible operating mode, the method comprises the step of exerting a translation action T4 on said distal rotational joint 457, so that to make said distal link 454 facing either a side or an opposite side of the robotic cart 477.

According to a possible operating mode, the method comprises the step of pivoting said macro-positioning arm 450 in respect to said robotic cart 477, preferably about a rotational joint having vertical axis.

The method comprises the step of repositioning said robotic cart 477 in respect to the operatory table 405, while maintaining said shared working volume 404 on or above the operatory bed 405.

By virtue of the features described above, provided either disjointed or in any combination thereof in particular embodiments, it is possible to respond to the above mentioned needs providing the above cited advantages, and in particular:

- the shafts of the surgical instruments converges towards one another;
- the shafts of the surgical instruments are not parallel to the sliders;
- the sliders of each motorized manipulator are respectively parallel;
- the shared working volume is maximized and approached frontally, from above and laterally by the distal end of the shafts, and by the end-effectors attached respectively thereto;
- the volumetric encumber of the slave part of the robot allows the surgeon to position him/her-self within the operatory arena such that both the microscope and the patient's anatomy are visible;
- the surgeon is allowed to switch from hand microsurgery to robot-aided microsurgery with minimum effort and without requiring him-her to seat/stand in another location;
- the surgeon is allowed to position either at the right or at the left side of the robotic cart;
- the passive [i.e. devoid of motorized degrees of freedom] macro-positioning arm can be moved also during surgery thanks to the brakes provided for at the rotational joints thereof;
- the slave part of the robot is made symmetric in respect of the vertical direction.

Those skilled in art may make many changes and adaptations to the embodiments described above or may replace elements with others which are functionally equivalent in order to satisfy contingent needs without however departing from the scope of the appended claims.

LIST OF REFERENCES

401 Robotic surgery assembly
402 Surgeon
402' Surgeon's shoulder
403, 503 Working volume
404 Shared working volume
405 Operatory table, or operatory bed
406 Master console assembly
407 Slave assembly
408 Operatory arena
410 Transmission component
411 First fixing portion of the transmission component
412 Second fixing portion of the transmission component
413 Plate
414 Thickness
415 Body of the transmission component, or component body
416 Proximal surface of the plate

417 Distal surface of the plate
418 Joint of the transmission component
419, 419' Bracket of the transmission component
420, 520 Motorized manipulator
421 Proximal fixing means
422 Distal fixing means
423 Second horizontal motorized slider
424 First horizontal motorized slider
425 Vertical motorized slider
426 Counterweight
427, 527 Case
428, 528 Proximal portion of the case
429, 529 Distal portion of the case
430, 530 Sterile adapter
431 Surgical drape
432 Draping assembly
433 Distal coupling portion of the sterile adapter
434 Window or passage
435 Polygonal perimeter
436 Corner portion of the top portion of the cart
437 First side of the cart
438 Second opposite side of the cart
439 Top portion of the cart
440, 540 Surgical instrument
441, 541 Shaft
442, 542 Distal end of the shaft
443 Field generator
444 Center portion of the distal link
445, 545 Attachment portion of the distal link
446 Telescopically extending portion
447 Robotic cart or tower
448 Ground contact unit, or wheel of the robotic cart
449 Handle of the robotic cart
450 Macro-positioning arm
451 Fixing portion of the motorized manipulator
452 Screen
453 Handle of the macropositioning arm
454 Distal link, of first link of the macropositioning arm
455 Second link of the macropositioning arm
456 Third link of the macropositioning arm
457 Distal rotational joint, or first joint of the macropositioning arm
458 Second rotational joint of the macropositioning arm
459 Third rotational joint of the macropositioning arm
460 Motor box assembly
461 Roll motor
462 Transmission belt
463 Sterile console
464 Surgical chair
465, 565 Master input tool
466, 566 Hand surgery tool
467 Master draping
468, 568 Resting element
469, 569 Cone of freedom
470 Microscope assembly
471 Image acquisition portion of the microscope
472 Vision device
473 Edge
474, 574 Dropping holster
476, 477, 478, 479 Links of the articulated terminal tool
480, 481, 482 Actuation cables of the articulated terminal tool
P Pitch
Y Yaw
G Grip
X-X First horizontal direction
Y-Y Second horizontal direction, or frontal direction
Z-Z Vertical direction
W-W Local proximal-distal direction
A1 Global surface area of the first fixing portion
A2 Global surface area of the at least one second fixing portion
G1 Geometric center of global surface area of the first fixing portion
G2 Geometric center of global surface area of the second fixing portion
d1 Offset distance of the transmission component
X2 Predefined horizontal distance
X4 First distance
X5 Second distance
P4 Pivoting action
T4 Translation action
Ω Solid angle

The invention claimed is:

1. A robotic surgery assembly for robotic-aided microsurgery comprising:

a macro-positioning passive arm;

a pair of motorized manipulators each comprising three mutually orthogonal motorized linear sliders, wherein the motorized linear sliders of one motorized manipulator of said pair are parallel to the motorized linear sliders of the other motorized manipulator of said pair; wherein both said motorized manipulators of said pair are attached to a same first link of the macro-positioning passive arm;

a pair of sterile adapters, each comprising a coupling device suitable for connecting to a surgical instrument;

a pair of surgical instruments respectively connected to said pair of sterile adapters, wherein each surgical instrument comprises a shaft; and a pair of transmission components wherein each transmission component of said pair comprises:

a first fixing portion configured to rigidly connect to a respective motorized manipulator of said pair of motorized manipulators;

a second fixing portion rigidly connecting to a respective sterile adapter of said pair of sterile adapters; and a component body between said first fixing portion and said second fixing portion holding in a respective mutual position said first fixing portion and said second fixing portion;

wherein:

said component body of each transmission component spaces said first fixing portion and said second fixing portion of an offset distance in a first horizontal direction, so that a manipulation action received from each motorized manipulator is transmitted shifted by said offset distance to the respective sterile adapter;

said component body of each transmission component comprises at least one rigidly locked joint providing an angular offset forming a solid angle in said first horizontal direction and in a second horizontal direction which is orthogonal to said first horizontal direction between said first fixing portion and said second fixing portion of the respective transmission component;

each transmission component is interposed between one motorized manipulator and the respective sterile adapter, to rigidly determine the relative mutual position and orientation of said three mutually orthogonal motorized linear sliders of the motorized manipulator and said coupling device of the respective sterile adapter;

the shaft of each surgical instrument is offset relative to each and all the sliding directions of said motorized linear sliders of the respective motorized manipulator;

the shafts of the two surgical instruments extend converging towards each other pointing with respective distal ends forward;

each motorized manipulator comprises a respective case individually encasing a respective motorized manipulator of said pair;

said cases are spaced from one another along said first horizontal direction by a predefined horizontal distance so that a window is delimited at least partially by said two cases;

said window is designed for a surgeon to occupy a position behind it so that the two motorized manipulators result positioned above the surgeon's shoulders;

said macro-positioning passive arm comprises a plurality of arm links including said same first link, said plurality of arm links being connected to one another in series and articulated through rotational joints, wherein said same first link to which said pair of motorized manipulators are attached further comprises two attachment portions, each attachment portion being configured to connect to one motorized manipulator of said pair of motorized manipulators;

a distal rotational joint connects said same first link and a second link of said plurality of arm links; and said distal rotational joint defines a rotational axis about which said same first link is pivotable, wherein a pivoting action pivoting the same first link about the rotational axis by a pivoting angle causes simultaneous circular motion of the pair of motorized manipulators around the rotational axis to thereby adjust a position of said pair of motorized manipulators relative to the second link of the macro-positioning passive arm.

2. The robotic surgery assembly of claim 1, further comprising at least one motor box assembly interposed between each respective transmission component and each respective sterile adapter and comprising a roll motor suitable for pivoting the respective surgical instrument with its shaft about the axis of longitudinal development of the shaft.

3. The robotic surgery assembly of claim 1, wherein a distal end of a first shaft reaches a first working volume and a distal end of a second shaft reaches a second working volume, wherein said first working volume and said second working volume are co-penetrated defining said shared working volume that can be reached by both distal portions of each shaft for any operative position of the sliders.

4. The robotic surgery assembly of claim 3, wherein said shared working volume is a parallelepiped.

5. The robotic surgery assembly of claim 1, wherein one of said motorized linear sliders of each motorized manipulator of said pair extends along a vertical direction.

6. The robotic surgery assembly of claim 1, wherein:

said predefined horizontal distance is greater than said offset distance;

each case of said cases encases at least one transmission component; and the two cases have a concave portion facing one another so that the shafts of the surgical instruments attached distally thereto converge one towards the other, both reaching said shared working volume with a distal end thereof.

7. The robotic surgery assembly of claim 1, wherein said first link of the macro-positioning passive arm and the pair of motorized manipulators form a reversed-"U"-shaped structure partially delimiting said window.

8. The robotic surgery assembly of claim 1, wherein the position of the attachment portions of the same first link are symmetrically arranged relative to the distal rotational joint.

9. The robotic surgery assembly of claim 1, wherein said macro-positioning passive arm is connected to a robotic cart having at least one ground contact unit.

10. The robotic surgery assembly of claim 9, wherein the cart comprises a top portion having a polygonal shape and defining a top portion perimeter forming a plurality of corner portions, wherein said macro-positioning passive arm is connected to near one of said corner portions.

11. The robotic surgery assembly of claim 10, wherein the top portion of the cart comprises a screen to display information on the state of the robotic surgery assembly.

12. The robotic surgery assembly of claim 1, further comprising a master controller assembly comprising at least one master input tool to control at least one of said surgical instruments and/or at least one of said motorized manipulators.

13. The robotic surgery assembly of claim 12, wherein the master controller assembly comprises a sterile console.

14. The robotic surgery assembly of claim 9, wherein said at least one ground contact unit comprises a plurality of wheels.

15. The robotic surgery assembly of claim 12, wherein the least one master input tool is mechanically unconstrained and is tracked by a tracking device.

16. The robotic surgery assembly of claim 15, wherein the tracking device is an optical and/or electromagnetic tracking device.

17. Operatory arena comprising:

at least one robotic surgery assembly of claim 1, an operatory table, and a microscope assembly, wherein at least one ocular of the microscope assembly is at least partially within said window.

* * * * *